(12) United States Patent
Friend

(10) Patent No.: US 11,419,835 B2
(45) Date of Patent: Aug. 23, 2022

(54) METHOD OF TREATMENT AND PREVENTION OF BACTERIAL VAGINOSIS

(71) Applicant: EVOFEM, INC., San Diego, CA (US)

(72) Inventor: David R. Friend, San Diego, CA (US)

(73) Assignee: Evofem, Inc., San Diego, CA (US)

( * ) Notice: Subject to any disclaimer, the term of this patent is extended or adjusted under 35 U.S.C. 154(b) by 0 days.

(21) Appl. No.: 16/338,977

(22) PCT Filed: Oct. 3, 2017

(86) PCT No.: PCT/US2017/054943
§ 371 (c)(1),
(2) Date: Apr. 2, 2019

(87) PCT Pub. No.: WO2018/067568
PCT Pub. Date: Apr. 12, 2018

(65) Prior Publication Data
US 2019/0224150 A1 Jul. 25, 2019

Related U.S. Application Data

(60) Provisional application No. 62/404,061, filed on Oct. 4, 2016.

(51) Int. Cl.
| | | |
|---|---|---|
| A61K 31/19 | (2006.01) | |
| A61K 9/00 | (2006.01) | |
| A61K 47/12 | (2006.01) | |
| A61K 47/38 | (2006.01) | |
| A61P 15/02 | (2006.01) | |

(52) U.S. Cl.
CPC ............ *A61K 31/19* (2013.01); *A61K 9/0034* (2013.01); *A61K 47/12* (2013.01); *A61K 47/38* (2013.01); *A61P 15/02* (2018.01)

(58) Field of Classification Search
CPC ........ A61K 31/19; A61K 47/12; A61K 47/38; A61K 9/0034; A61K 47/36; A61K 9/06; A61P 15/02
See application file for complete search history.

(56) References Cited

U.S. PATENT DOCUMENTS

| | | | |
|---|---|---|---|
| 4,999,342 A | 3/1991 | Ahmad et al. | |
| 5,617,877 A | 4/1997 | Moench et al. | |
| 5,667,492 A | 9/1997 | Bologna et al. | |
| 6,468,526 B2 | 10/2002 | Chrisope | |
| 6,664,296 B1 | 12/2003 | Meignant | |
| 6,706,276 B2 | 3/2004 | Garg et al. | |
| 8,425,894 B2 | 4/2013 | Batcheller et al. | |
| 8,518,378 B2 | 8/2013 | Tamarkin et al. | |
| 8,871,244 B2 | 10/2014 | Andersch | |
| 9,060,933 B2 | 6/2015 | Dahl | |
| 9,198,858 B2 | 12/2015 | Nordsiek et al. | |
| 9,566,232 B2 | 2/2017 | Guthrie | |
| 10,568,855 B2 | 2/2020 | Guthrie | |
| 2002/0177624 A1 | 11/2002 | Hanna et al. | |
| 2004/0009223 A1 | 1/2004 | Garg et al. | |
| 2004/0242459 A1 | 12/2004 | Forrest et al. | |
| 2005/0272700 A1 | 12/2005 | Buyuktimkin et al. | |
| 2006/0105008 A1 | 5/2006 | Ahmad | |
| 2008/0153776 A1 | 6/2008 | Xia et al. | |
| 2009/0142313 A1 | 6/2009 | Talling et al. | |
| 2010/0069323 A1 | 3/2010 | Seto et al. | |
| 2011/0020265 A1 | 1/2011 | Batcheller et al. | |
| 2011/0104262 A1 | 5/2011 | Lulla et al. | |
| 2011/0132376 A1 | 6/2011 | Dahl | |
| 2011/0159091 A1 | 6/2011 | Stone et al. | |
| 2012/0070476 A1* | 3/2012 | Moench | A61K 9/0036 424/400 |
| 2013/0005785 A1 | 1/2013 | Nordsiek | |
| 2013/0005787 A1 | 1/2013 | Nordsiek et al. | |
| 2013/0150810 A1 | 6/2013 | Maguire et al. | |
| 2015/0080467 A1 | 3/2015 | Andersch | |
| 2015/0164837 A1* | 6/2015 | Abels | A61K 31/205 514/563 |
| 2015/0202216 A1* | 7/2015 | Guthrie | A61P 31/18 514/81 |
| 2016/0008276 A1 | 1/2016 | Guthrie | |
| 2016/0136193 A1 | 5/2016 | Hansen | |
| 2016/0354394 A1 | 12/2016 | Guthrie et al. | |
| 2017/0128396 A1 | 5/2017 | Guthrie | |
| 2019/0133978 A1 | 5/2019 | Guthrie | |
| 2019/0209502 A1 | 7/2019 | Friend | |
| 2020/0147015 A1 | 5/2020 | Guthrie | |

FOREIGN PATENT DOCUMENTS

| | | |
|---|---|---|
| AU | 2015201042 A1 | 9/2015 |
| CN | 1431895 A | 7/2003 |
| EP | 0255902 A1 | 2/1988 |
| JP | S6379816 A | 4/1988 |
| JP | H02104517 A | 4/1990 |

(Continued)

OTHER PUBLICATIONS

Elgantri et. al., Sebha Medical Journal, 2010, vol. 9(1), pp. 20-27 (Year: 2010).*
Keller, et al., Phase 1 randomized safety study of twice daily dosing of acidform vaginal gel: Candidate antimicrobial contraceptive, PLOS One, 2012, 11 pages, vol. 7. No. 10.
Apr. 2004) Genital HPV Infection—Fact Sheet, Available at: https://www.cdc.gov/std/hpv/stdfact-hpv.htm, 4 Pages.
1967) Physical Properties of Glycerine and Its Solutions, Gulf Publishing Company, 27 pages.
Apr. 2004) Saved 3,048 times between Apr. 4, 2004 and May 28, 2020, Available at: https://web.archive.org/web/20040801000000*/https://www.cdc.gov/std/hpv/stdfact-hpv.htm, 2 Pages.
Asada et al. (1997) "Inhibitory Effect of Alginic Acids on Hyaluronidase and on Histamine Release from Mast Cells", Bioscience, Biotechnology, and Biochemistry, 61(6):1030-1032.

(Continued)

*Primary Examiner* — Sarah Pihonak
(74) *Attorney, Agent, or Firm* — Mintz Levin Cohn Ferris Glovsky and Popeo, P.C.

(57) ABSTRACT

Described herein are methods of reducing the risk of recurrence of bacterial vaginosis by intravaginal administration of compositions comprising L-lactic acid, polymer thickener, and preservative.

21 Claims, 5 Drawing Sheets

(56) References Cited

FOREIGN PATENT DOCUMENTS

| | | |
|---|---|---|
| JP | 3202365 B2 | 12/1992 |
| JP | H06172375 A | 6/1994 |
| JP | H10507178 A | 7/1998 |
| JP | H11501292 A | 2/1999 |
| JP | 2009102407 A | 5/2009 |
| JP | 6352907 B2 | 7/2015 |
| KR | 1020100016060 A | 2/2010 |
| RU | 2257197 C1 | 7/2005 |
| WO | 9610989 A1 | 4/1996 |
| WO | 9619195 A1 | 6/1996 |
| WO | 0138284 A1 | 5/2001 |
| WO | WO 2001/66084 | 9/2001 |
| WO | 03000224 A1 | 1/2003 |
| WO | 2004011032 A1 | 2/2004 |
| WO | 2008119518 A1 | 10/2008 |
| WO | 2009155118 A1 | 12/2009 |
| WO | 2010138823 A1 | 12/2010 |
| WO | 2010142761 A1 | 12/2010 |
| WO | 2012151237 A1 | 11/2012 |
| WO | 2013187984 A1 | 12/2013 |
| WO | WO 2014/041378 | 3/2014 |
| WO | 2015027071 A1 | 2/2015 |
| WO | WO 2015/070072 | 5/2015 |
| WO | WO 2015/095793 | 6/2015 |
| WO | 2018049326 A1 | 3/2018 |

OTHER PUBLICATIONS

Auras et al. (2010) "Poly(lactic acid): Synthesis, Structures, Properties, Processing, and application", John Wiley & Sons: Hobken, 3 pages.
Cyber Colloids, Ltd. (1978) "The History of Alginate Chemistry—Bacterial", Available at http://www.cybercolloids.net/information/technical-articles/history-alginate-chemistry-structure, 1 page.
Dien et al. (2001) "Recombinant *Eshcerichia coli* Engineered for Production of L-lactic Acid from Hexose and Pentose Sugars", J. Ind Microbiol Biotechnol, 27(4):259-264.
Donati et al. (2009) "Material Properties of Alginates", Biology and Applications, 53 pages.
Draget et al. (2005) "Alginates from Algae", Peptide Science 6, 30 pages.
Dumitriu et al. (1996) "Ed. Polysaccharides in Medicinal applications", Marcel Dekker, Inc., 622:3 pages.
Esseco Group (2005) "Potassium Bitartarate", Material Safety Data Sheet, 4 pages.
Fisher Scientific (Mar. 19, 2002) "Citric acid", Available at: https://fscimage.fishersci.com/msds/05200.htm, 6 pages.
Flemming et al. (2003) "The Crucial Role of Extracellular Polymeric Substances in Biofilms. Biofilms in Wastewater Treatment: an Interdisciplinary approach", Wuertz, Bishop, Wilderer, eds., IWA Publishing, 181-187.
Higgins Chris (Oct. 2011) "L-lactate and D-lactate—Clinical Significance of the Difference", Acutecaretesting.org, 7 Pages.
Ishida et al. (2005) "Efficient production of I-Lactic acid by metabolically engineered *Saccharomyces cerevisiae* with a genome-integrated L-lactate dehydrogenase gene", Appl. Environ Microbiol., 7(4): 1964-1970.
Jeong et al. (Jun. 2006) "Alginic Acid has Anti Anaphylactic Effects and Inhibits Inflammatory Cytokine Expression via Suppression of Nuclear Factor-KappaB Activation", Clinical and Experimental allergy, 36(6):785-794.
Jungbunzlauer Inc. (2008) "Xanthan Gum Food Grade", Material Safety Data Sheet, 4 pages.
Lee et al. (Jan. 2012) "Alginate: Properties and Biomedical Applications", Progress in Polymer Science, 37 (1):106-126.
Leitch et al. (2002) "*Escherichia coli* O157 and Non-O157 Isolates Are More Susceptible to L-Lactate than to D-Lactate", Applied and Environmental Microbiology, 68(9):4676-4678.
Lide et al. (1995) "Handbook of Data on Common Organic Compounds", CRC Press: Boca Raton, 503-505.
Malinova (2009) "Lactobor Intim Vaginal gel for the Treatment and Prevention of Bacterial Vaginosis", Akush Ginekol (Sofiia) (English translation), 48(Suppl. 2):3 pages.
O'Hanlon et al. (Jul. 19, 2011) "In Vaginal Fluid, Bacteria associated with Bacterial Vaginosis can be Suppressed with Lactic Acid but not Hhydrogen Peroxide", BMC Infectious Diseases, 1(200):8 pages.
Owen et al. (Jul. 27, 1905) "A Review of the Physical and Chemical Properties of Human Semen and the Formulation of a Semen Simulant", Journal of Andrology, 26(4):459-469.
Owen et al. (Jun. 28, 1999) "Factors Influencing Nonoxynol-9 Permeation and Bioactivity in Cervical Mucus", Journal of Controlled Release, 60(1):23-34.
Pande et al. (Aug. 2003) "Nuclear Factor Kappa B: a Potential Target for Anti-HIV Chemotherapy", Current Medicinal Chemistry, 10(16):1603-1615.
Purcell et al. (2012) "Biology of Mucosally Transmitted Sexual Infection—Translating the Basic Science into Novel HIV Intervention: A Workshop Summary", AIDS Research and Human Retroviruses, 28(11):1389-1396.
Rehan et al. (Jun. 6, 1975) "The Semen of Fertile Men: Statistical Analysis of 1300 Men", Fertility and Sterility, 26(6):492-502.
Segeren et al. (1974) "Rheological and Swelling Behaviour of Alginate Gels", Faraday Discussions of the Chemical Society, 57:255-262.
Unknown Author (2020) "Wayback Machine", 2 pages.
Urb et al. (Apr. 2012) "The Role of Mast Cells in the Defense against Pathogens", PLoS Pathogens, e1002619, 8 (4):3 pages.
Zhang et al. (Nov. 2011) "pH-responsive Nanoparticles Releasing Tenofovir Intended for the Prevention of HIV Transmission", European Journal of Pharmaceutics and Biopharmaceutics, 79(3):25 Pages.
Aldunate et al. (May 8, 2013) "Vaginal Concentrations of Lactic Acid Potently Inactivate HIV", Antimicrob Chemother, 68:2015-2025.
Morris Sheldonr (2021) "Human Papillomavirus (HPV) Infection", Merck Manuals, https://www.merckmanuals.com/home/infections/sexually-transmitted-diseases-stds/human-papillomavirus-hpv-infection#, 3 pages.

* cited by examiner

METHOD OF TREATMENT AND PREVENTION OF BACTERIAL VAGINOSIS

CROSS-REFERENCE

This application is a 371 national stage entry of International Patent Application PCT/US2017/054943, filed Oct. 3, 2017, which claims the benefit of U.S. Provisional Application No. 62/404,061 filed Oct. 4, 2016, each of which is incorporated by reference herein in its entirety.

BACKGROUND OF THE DISCLOSURE

There is a need for developing compositions and methods for improved treatment and prevention of bacterial vaginosis (BV).

SUMMARY OF THE DISCLOSURE

Disclosed herein, in some embodiments, are methods of treating bacterial vaginosis (BV) comprising intravaginally administering a composition to a subject with a BV, wherein the composition comprises: (a) a polymer thickener; (b) L-lactic acid; and (c) a preservative, wherein administering the composition ameliorates symptoms of BV in the subject. In some instances, the polymer thickener is selected from a group consisting of xanthan gum, alginic acid, hydroxypropyl cellulose, hydroxypropyl methyl cellulose, sodium carboxymethyl cellulose, chitosan, polycarbophil, and carbopol. In some instances, the composition further comprises a humectant. In some instances, the composition further comprises at least one of a pharmaceutically acceptable carrier, water, and a buffer. In some instances, the buffer comprises citric acid and potassium bitartrate. In some instances, the composition is administered once or multiple times during a course of treatment. In some instances, the course of treatment comprises about 1 week to about 20 weeks. In some instances, the course of treatment comprises an initial course of treatment and a subsequent course of treatment and wherein the composition is administered more frequently during the initial course of treatment than during the subsequent course of treatment. In some instances, the frequency of administration during the initial course of treatment is daily, less than once daily, every other day, once a week, or once every 2 weeks. In some instances, the frequency of administration during the subsequent course of treatment is less than once daily, every other day, once a week, once every 2 weeks, or once every 3 weeks. In some instances, the composition is administered at a dosage from about 0.5 g to about 10 g, from about 3 g to about 5 g, about 3 g, about 4 g, or about 5 g. In some instances, administration of the composition lowers vaginal pH of the subject, thereby treating the BV. In some instances, administration of the composition restores a healthy vaginal microbiome in the subject, thereby treating the BV. In some instances, the subject has previously been diagnosed as Amsel-positive. In some instances, upon of administration of the composition the subject is Amsel-negative, thereby treating the BV.

Disclosed herein, in some embodiments, is a method of reducing the recurrence rate of bacterial vaginosis (BV) comprising intravaginally administering a composition to a subject, wherein the composition comprises: (a) a polymer thickener; (b) L-lactic acid; and (c) a preservative, wherein administering the composition reduces recurrence rate of bacterial vaginosis in the subject. In some instances, the subject is a subject with BV. In some instances, the subject with BV is asymptomatic In some instances, the subject is free of bacterial vaginosis (BV). In some instances, the polymer thickener is selected from a group consisting of xanthan gum, alginic acid, hydroxypropyl cellulose, hydroxypropyl methyl cellulose, sodium carboxymethyl cellulose, chitosan, polycarbophil, and carbopol. In some instances, the composition further comprises a humectant. In some instances, the composition further comprises at least one of a pharmaceutically acceptable carrier, water, and a buffer. In some instances, the buffer comprises citric acid and potassium bitartrate. In some instances, the composition is administered once or multiple times during a course of treatment. In some instances, the course of treatment comprises about 1 week to about 20 weeks. In some instances, the course of treatment comprises an initial course of treatment and a subsequent course of treatment and wherein the composition is administered more frequently during the initial course of treatment than during the subsequent course of treatment. In some instances, the frequency of administration during the initial course of treatment is daily, less than once daily, every other day, once a week, or once every 2 weeks. In some instances, the frequency of administration during the subsequent course of treatment is less than once daily, every other day, once a week, once every 2 weeks, or once every 3 weeks. In some instances, the composition is administered at a dosage from about 0.5 g to about 10 g, from about 3 g to about 5 g, about 3 g, about 4 g, or about 5 g. In some instances, administration of the composition lowers vaginal pH of the subject, thereby reducing the recurrence rate of the BV. In some instances, administration of the composition lowers vaginal pH of the subject, thereby reducing the recurrence rate of the BV. In some instances, administration of the composition restores a healthy vaginal microbiome in the subject, thereby reducing the recurrence rate of the BV. In some instances, the subject has previously been diagnosed as Amsel-positive. In some instances, upon of administration of the composition the subject is Amsel-negative, thereby reducing the recurrence rate of the BV.

In one embodiment is provided a method of treating bacterial vaginosis (BV) comprising intravaginally administering a composition to a subject with BV, wherein the composition comprises: (a) a polymer thickener; (b) L-lactic acid; and (c) a preservative, wherein administering the composition ameliorates symptoms of BV in the subject. In another embodiment is provided a method of reducing the recurrence rate of bacterial vaginosis (BV) comprising intravaginally administering a composition to a subject with BV, wherein the composition comprises: (a) a polymer thickener; (b) L-lactic acid; and (c) a preservative, wherein administering the composition reduces recurrence rate of bacterial vaginosis in the subject. Yet another embodiment provides a method of preventing the recurrence of bacterial vaginosis (BV) comprising intravaginally administering a composition to a subject with BV, wherein the composition comprises: (a) a polymer thickener; (b) L-lactic acid; and (c) a preservative, wherein administering the composition prevents recurrence of bacterial vaginosis in the subject. In some embodiments, the preservative is selected from a group consisting of benzoic acid, sodium benzoate, methylparaben, ethylparaben, butyulparaben, propylparaben, benzyalkonium chloride, phenylmercuric nitate, and chlorhexidine. In some embodiments, the polymer thickener is selected from a group consisting of xanthan gum, alginic acid, hydroxypropyl cellulose, hydroxypropyl methyl cellulose, sodium carboxymethyl cellulose, chitosan, polycarbophil, and carbopol. In some embodiments, the polymer thickener is a combination of xanthan gum and alginic acid. In some embodiments, the composition further comprises a humectant. In some embodiments, the humectant is selected from a group consisting of glycerol, polyethylene glycol, propylene glycol, sorbitol, and tiracetin. In some embodiments, the composition further comprises a pharmaceutically acceptable carrier. In some embodiments, the composition further comprises water. In some embodiments, the composition further comprises a buffer. In some embodiments, the buffer comprises citric acid and potassium bitartrate.

In some embodiments, the composition is administered once during a course of treatment. In some embodiments, the composition is administered multiple times during a course of treatment. In some embodiments, the course of treatment comprises an initial course of treatment and a subsequent course of treatment and wherein the composition is administered more frequently during the initial course of treatment than during the subsequent course of treatment. In some embodiments, the initial course of treatment is between 1 week and 4 weeks. In some embodiments, the initial course of treatment is about 2 weeks to about 3 weeks. In some embodiments, the initial course of treatment is about 1 week. In some embodiments, the subsequent course of treatment is about 1 week to about 19 weeks. In some embodiments, the subsequent course of treatment is about 2 weeks to about 18 weeks. In some embodiments, the subsequent course of treatment is about 3 weeks to about 17 weeks. In some embodiments, the subsequent course of treatment is about 4 weeks to about 16 weeks. In some embodiments, the subsequent course of treatment is 5 weeks to about 15 weeks. In some embodiments, the subsequent course of treatment is about 6 weeks to about 14 weeks. In some embodiments, the subsequent course of treatment is about 7 weeks to about 13 weeks. In some embodiments, the subsequent course of treatment is about 8 weeks to about 12 weeks. In some embodiments, the subsequent course of treatment is about 9 weeks to about 10 weeks. In some embodiments, the subsequent course of treatment is about 10 weeks to about 11 weeks. In some embodiments, the frequency of administration during the initial course of treatment is daily. In some embodiments, the frequency of administration during the initial course of treatment is every other day. In some embodiments, the frequency of administration during the initial course of treatment is once a week. In some embodiments, the frequency of administration during the initial course of treatment is once every 2 weeks. In some embodiments, the frequency of administration during the subsequent course of treatment is every other day. In some embodiments, the frequency of administration during the initial course of treatment is once every week. In some embodiments, the frequency of administration during the initial course of treatment is once every 2 weeks. In some embodiments, the frequency of administration during the initial course of treatment is once every 3 weeks. In some embodiments, the composition is administered at a dosage from about 0.5 g to about 10 g. In some embodiments, the composition is administered at a dosage from about 3 g to about 5 g. In some embodiments, the composition is administered at a dosage selected from about 3 g, about 4 g, and about 5 g.

A further embodiment provides a method of prognosis for risk of recurrence of bacterial vaginosis (BV) in a subject with BV, the method comprising (a) testing vaginal pH of the subject; (b) intravaginally administering a composition as defined in any one of the aforementioned embodiments to the subject, (c) re-testing vaginal pH of the subject; and (d) prognosing risk of recurrence of BV based on comparing the results of the vaginal pH tests in step (a) and (c). Another embodiment provides a method of prognosis for risk of recurrence of bacterial vaginosis (BV) in a subject with BV, the method comprising (a) analyzing vaginal microbiome of the subject; (b) intravaginally administering a composition as defined in any of the aforementioned embodiments to the subject, (c) re-analyzing vaginal microbiome of the subject; and (d) prognosing risk of recurrence of BV based on comparing the results of the vaginal microbiome analyses in step (a) and (c). Yet another embodiment provides a method of prognosis for risk of recurrence of bacterial vaginosis (BV) in a subject, the method comprising (a) assessing BV in a subject using Amsel criteria; (b) intravaginally administering a composition as defined in any one of the aforementioned embodiments to the subject, (c) re-assessing BV in the subject using Amsel criteria; and (d) prognosing risk of recurrence of BV based on comparing the assessments in step (a) and (c). In some embodiments, the composition is administered once during a course of treatment. In some embodiments, the composition is administered multiple times during a course of treatment. In some embodiments, the course of treatment comprises an initial course of treatment and a subsequent course of treatment and wherein the composition is administered more frequently during the initial course of treatment than during the subsequent course of treatment. In some embodiments, the initial course of treatment is between 1 week and 4 weeks. In some embodiments, the initial course of treatment is about 2 weeks to about 3 weeks. In some embodiments, the initial course of treatment is about 1 week. In some embodiments, the subsequent course of treatment is about 1 week to about 19 weeks. In some embodiments, the subsequent course of treatment is about 2 weeks to about 18 weeks. In some embodiments, the subsequent course of treatment is about 3 weeks to about 17 weeks. In some embodiments, the subsequent course of treatment is about 4 weeks to about 16 weeks. In some embodiments, the subsequent course of treatment is 5 weeks to about 15 weeks. In some embodiments, the subsequent course of treatment is about 6 weeks to about 14 weeks. In some embodiments, the subsequent course of treatment is about 7 weeks to about 13 weeks. In some embodiments, the subsequent course of treatment is about 8 weeks to about 12 weeks. In some embodiments, the subsequent course of treatment is about 9 weeks to about 10 weeks. In some embodiments, the subsequent course of treatment is about 10 weeks to about 11 weeks. In some embodiments, the frequency of administration during the initial course of treatment is daily. In some embodiments, the frequency of administration during the initial course of treatment is every other day. In some embodiments, the frequency of administration during the initial course of treatment is once a week. In some embodiments, the frequency of administration during the initial course of treatment is once every 2 weeks. In some embodiments, the frequency of administration during the subsequent course of treatment is every other day. In some embodiments, the frequency of administration during the initial course of treatment is once every week. In some embodiments, the frequency of administration during the initial course of treatment is once every 2 weeks. In some embodiments, the frequency of administration during the initial course of treatment is once every 3 weeks. In some embodiments, the composition is administered at a dosage from about 0.5 g to about 10 g. In some embodiments, the composition is administered at a dosage from about 3 g to about 5 g. In some embodiments, the composition is administered at a dosage selected from about 3 g, about 4 g, and about 5 g. In some embodiments, the lowering of vaginal pH between steps (a) and (c) is associated with good prognosis for reduced risk of recurrence of BV. In some embodiments, the restoration of a healthy vaginal microbiome between steps (a) and (c) is associated with good prognosis for reduced risk of recurrence of BV. In some embodiments, the assessment result is Amsel-positive or Amsel-negative in the steps (a) and (c). In some embodiments, the change in assessment result from Amsel-positive to Amsel-negative between steps (a) and (c) is associated with good prognosis for reduced risk of recurrence of BV.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE DISCLOSURE

Figure 1:
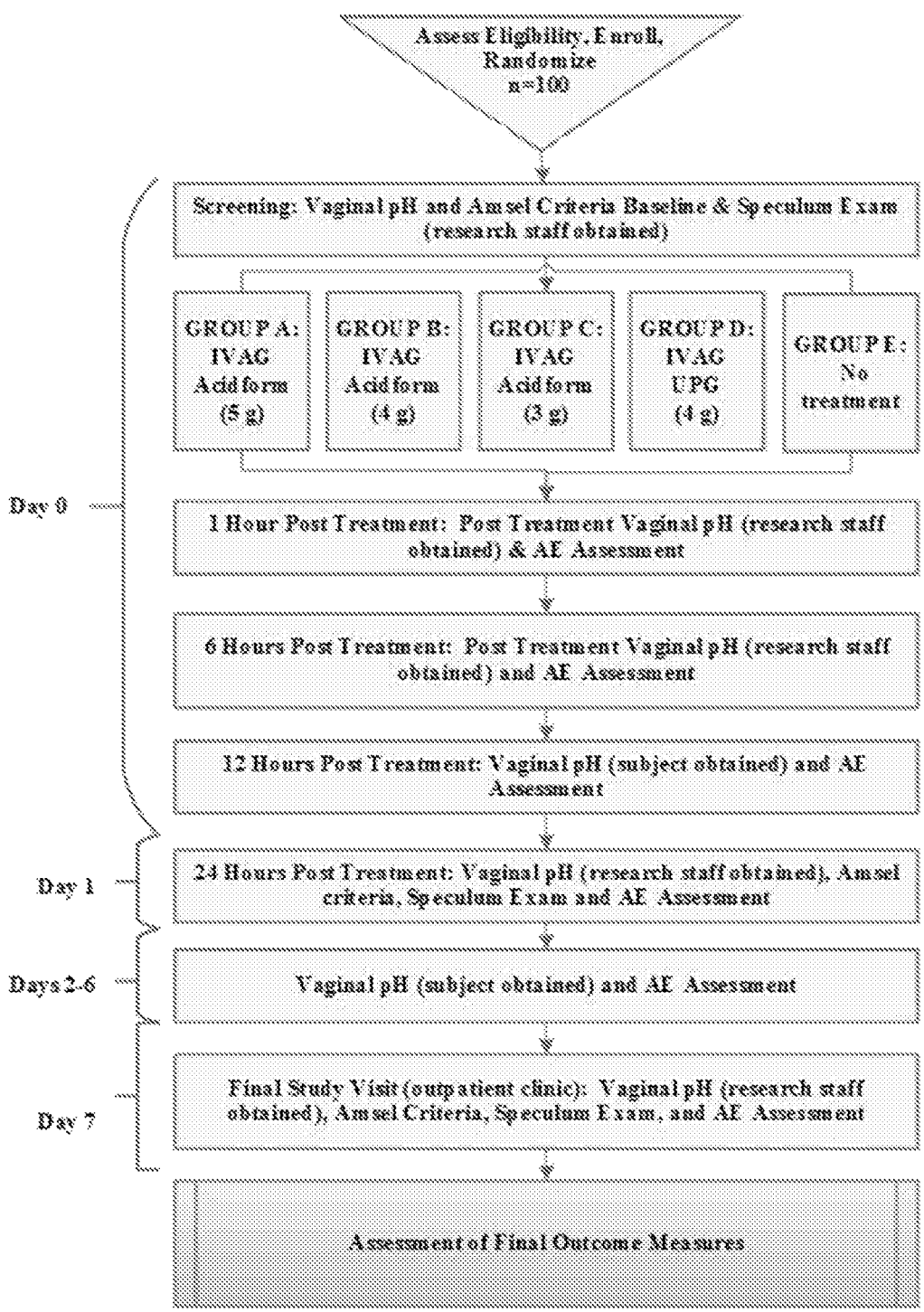
FIG. 1 illustrates an exemplary study design for a phase 1 randomized placebo controlled pilot study to determine the effect and duration of an intravaginal composition, as described in the present disclosure, on vaginal pH.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments of the present disclosure described herein may be employed. It is intended that the following claims define the scope of the present disclosure and that methods and structures within the scope of these claims and their equivalents be covered thereby.

Unless defined otherwise, all technical and scientific terms used herein have the same meaning as commonly understood by one of skill in the art to which the present disclosure described herein belong. All publications, patents, and patent applications mentioned in this specification are hereby incorporated by reference to the same extent as if each individual publication, patent, or patent application was specifically and individually indicated to be incorporated by reference.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The terminology used herein is for the purpose of describing particular cases only and is not intended to be limiting. As used herein, the singular forms "a", "an" and "the" include the plural forms as well, unless the context clearly indicates otherwise. Furthermore, to the extent that the terms "contains," "containing," "including", "includes," "having," "has", "with", or variants thereof are used in either the detailed description and/or the claims, such terms are intended to be inclusive in a manner similar to the term "comprising."

The term "about" or "approximately" are meant to refer to values within an acceptable error range for the particular value as determined by one of ordinary skill in the art, which will depend in part on how the value is measured or determined, e.g., the limitations of the measurement system. For example, "about" means, in some cases, within 1 or more than 1 standard deviation, per the practice in the given value. Where particular values are described in the application and claims, unless otherwise stated the term "about" should be assumed to mean an acceptable error range for the particular value, such as ±10% of the value modified by the term "about".

The terms "treat," "treating," and "treatment" include alleviating or abrogating a disorder, disease, or condition; or one or more of the symptoms associated with the disorder, disease, or condition; or alleviating or eradicating the cause(s) of the disorder, disease, or condition itself. Desirable effects of treatment include, but are not limited to, preventing occurrence or recurrence of disease, alleviation of symptoms, diminishing any direct or indirect pathological consequences of the disease, preventing metastasis, decreasing the rate of disease progression, amelioration or palliation of the disease state and remission or improved prognosis. The terms "prevent," and "preventing," include reducing the likelihood of occurrence of a disease, disorder, or condition.

The term "subject with bacterial vaginosis (By)" includes subjects who currently or previously had BV. In some instances, the subject currently has BV but is asymptomatic. In some instances, the subject is currently free of BV due to previously administered treatment for BV, such as, for example, antibiotics.

Bacterial Vaginosis

Bacterial vaginosis (BV) is a common condition characterized by dysbiosis of the vaginal microbiota, such that the proportion of lactic acid-producing bacteria, primarily *Lactobacillus* sp., is greatly reduced and the number and diversity of facultative and strictly anaerobic bacteria, including species of *Gardnerella, Prevotella* and other Clostridialis taxa, and Gram-positive cocci, including *Enterococcus faecalis*, is greatly increased. Studies have shown that the microbial flora of the vagina, i.e., its microbiome, is usually affected by the pH of the vaginal fluid, such that a lower (more acidic) pH favors *Lactobacillus* sp., whereas a higher (more basic) pH favors anaerobic organisms that are associated with BV. BV is typically associated with a vaginal pH>5, elevated vaginal levels of Interleukin-6 (IL-6), a proinflammatory cytokine, increased risk of *Neisseria gonorrhoeae, Chlamydia trachomatis, Trichomonas vaginalis* and herpes simplex virus (HSV) type 2 infections, preterm delivery and low birth weight infants. Treatment with antibiotics often fails to correct the microflora imbalance, and recurrence of BV is common. Accordingly, there is need for an improved treatment of BV to reduce the risk of recurrence. The present disclosure provides a method of treating or preventing BV by administration of a composition described herein, such that the risk of recurrence of BV is reduced following administration of the composition.

BV is clinically identified if at least three of the following four Amsel criteria are met: 1) thin, gray/white discharge; 2) malodorous "fishy" discharge upon adding 10% potassium hydroxide to vaginal secretions (also referred to as "whiff test"; 3) high vaginal pH (>4.5), and 4) identification of vaginal epithelial cells heavily coated with bacteria (i.e., "clue cells"). In the present disclosure, a subject is defined as Amsel-positive if the subject meets at least three out of the four Amsel criteria. Further, in the present disclosure a subject is defined as Amsel-negative if the subject does not meet at least three out of the four Amsel criteria.

Methods of Treatment

Provided herein in one embodiment is a method of treating or preventing BV comprising intravaginally administering a composition comprising: (a) a polymer thickener, (b) L-lactic acid, and (b) a preservative. In some embodiments, the method described herein comprises intravaginally administering to a subject a composition comprising (a) a polymer thickener; (b) L-lactic acid; and (c) a preservative, wherein administering the composition reduces the risk of recurrence of BV in the subject.

In some embodiments, the composition comprises about 1% to about 10% L-lactic acid. In some embodiments, the composition comprises about 1% to about 9% L-lactic acid. In some embodiments, the composition comprises about 1% to about 8% L-lactic acid. In some embodiments, the composition comprises about 1% to about 7% L-lactic acid. In some embodiments, the composition comprises about 1% to about 6% L-lactic acid. In some embodiments, the composition comprises about 1% to about 5% L-lactic acid. In some embodiments, the composition comprises about 1% to about 4% L-lactic acid. In some embodiments, the composition comprises about 1% to about 3% L-lactic acid. In some embodiments, the composition comprises about 1% to about 2% L-lactic acid. In some embodiments, the composition comprises about 1% to about 1.5% L-lactic acid. The percent unit of the components refers to % weight/weight (% w/w).

In some embodiments, the composition comprises (a) about 0.1% to about 10% of a polymer thickener, (b) about 1% to about 10% L-lactic acid, and (c) about 0.1% to about 10% of a preservative. In certain embodiments, the composition comprises, (a) about 1% to about 7% of a polymer thickener, (b) about 1% to about 10% L-lactic acid, and (c) about 0.1% to about 2% of a preservative. In some embodiments, the composition comprises (a) about 1.5% to about 8% of a polymer thickener, (b) about 1% to about 5% L-lactic acid, and (c) about 0.1% to about 0.5% of a preservative. In certain embodiments, the composition comprises (a) about 2% to about 5% of a polymer thickener, (b) about 1% to about 2.5% L-lactic acid, and (c) about 0.2% to about 0.4% of a preservative. In certain embodiments, the composition comprises (a) about 2.5% to about 4.5% of a polymer thickener, (b) about 1% to about 2% L-lactic acid, and (c) about 0.1% to about 0.2% of a preservative. In certain embodiments, the composition comprises (a) about 6.25% of a polymer thickener, (b) about 1% L-lactic acid, and (c) about 0.2% of a preservative. In certain embodiments, the composition comprises (a) about 5.25% of a polymer thickener, (b) about 1% L-lactic acid, and (c) about 0.2% of a preservative.

Non-limiting examples of polymer thickeners include alginic acid, chitosan, gellan gum, xanthan gum, poloxamer, hydroxypropyl cellulose, hydroxypropyl methyl cellulose, sodium carboxymethyl cellulose, polycarbophil, carbopol and the like. In some embodiments, the polymer thickener is alginic acid and xanthan gum. In some embodiments, the polymer thickener is alginic acid. Alginic acid is a generally linear glycouronan polymer containing a mixture of polysaccharide polymer of beta-D-mannuronate and alpha-L-guluronate residues. The molecular weight of the alginic acid, in some instances, is in the range of about 20,000 to about 300,000 g/mole, about 20,000 to about 250,000 g/mole, about 240,000 g/mole, about 25,000 to about 30,000 g/mole, about 30,000 to about 35,000 g/mole, about 35,000 to about 40,000 g/mole, about 40,000 to about 45,000 g/mole, about 45,000 to about 50,000 g/mole, about 50,000 to about 55,000 g/mole, about 55,000 to about 60,000 g/mole, about 60,000 to about 65,000 g/mole, about 65,000 to about 70,000 g/mole, about 70,000 to about 75,000 g/mole, about 75,000 to about 80,000 g/mole, about 80,000 to about 85,000 g/mole, about 85,000 to about 90,000 g/mole, about 95,000 to about 100,000 g/mole, about 125,000 to about 150,000 g/mole, about 150,000 to about 200,000 g/mole, or about 100,000 to about 200,000 g/mole. The average molecular weight of the alginic acid is, in some instances, in the range of about 20,000 to about 300,000 Da, about 20,000 to about 250,000 Da, about 240,000 Da, about 25,000 to about 30,000 Da, about 30,000 to about 35,000 Da, about 35,000 to about 40,000 Da, about 40,000 to about 45,000 Da, about 45,000 to about 50,000 Da, about 50,000 to about 55,000 Da, about 55,000 to about 60,000 Da, about 60,000 to about 65,000 Da, about 65,000 to about 70,000 Da, about 70,000 to about 75,000 Da, about 75,000 to about 80,000 Da, about 80,000 to about 85,000 Da, about 85,000 to about 90,000 Da, about 95,000 to about 100,000 Da, about 125,000 to about 150,000 Da, about 150,000 to about 200,000 Da, or about 100,000 to about 200,000 Da, about 180,000 Da, about 183,855 Da, about 185,000 Da, about 190,000 Da, or about 195,000 Da. In certain examples, the alginic acid comprises guluronic acid (G) and mannuronic acid (M) residues or units. In some instances, the alginic acid comprises about 65-75% G residues and about 25-35% M residues. The ratio between the M and G residues, are in some examples, from about 0.1 to 0.2, about 0.2 to about 0.3, about 0.3 to about 0.4, about 0.4 to about 0.5, about 0.5 to about 0.6, about 0.6 to about 0.7, about 0.7 to about 0.8, about 0.8 to about 1, about 0.2, about 0.21, about 0.22, about 0.23, about 0.24, about 0.25, about 0.26, about 0.27, about 0.28, about 0.29, about 0.30, about 0.31, about 0.32, about 0.33, about 0.34, about, 0.35, about 0.36, about 0.37, about 0.39, about 0.39, about 0.40, about 0.41, about 0.42, about 0.43, about 0.44, about 0.45, about 0.46, about 0.47, about 0.48, about 0.49, or about 0.5.

Alginic acid forms insoluble alginates by interacting with monovalent and divalent cations (especially $Na^+$, $K^+$, and $Ca^{++}$) in seminal plasma. Alginates also swell in contact with water, thereby assisting in maintaining the gel form of the composition within the vagina. It is also contemplated that alginic acid or salts of alginic acid contribute to the acid buffering activity of the composition since they have a pH of about 1.5 to about 3.5 in an aqueous solution. Furthermore, in some embodiments the alginic acid acts as a bioadhesive and provides the composition with bioadhesive properties. Without being bound by any particular theory, it is believed that because of its high molecular weight, alginic acid is not absorbed by the body. Thus, its effect as a polymer thickener, a bioadhesive, and acid-buffering agent is maintained so as long as the gel remains in the vagina. In some embodiments, the polymer thickener is xanthan gum. In some embodiments, the polymer thickener is a combination of xanthan gum and alginic acid. In some embodiments, the alginic acid is PROTACID F120.

The composition, in some embodiments, further comprises a bioadhesive compound. Non-limiting examples of bioadhesive compounds include, xanthan gum, hydroxypropyl cellulose, hydroxypropyl methyl cellulose, sodium carboxymethyl cellulose, chitosan, polycarbophil, carbopol, and the like. In some embodiments, the bioadhesive compound is xanthan gum, a high molecular weight polysaccharide gum containing D-glucosyl, D-mannosyl, and D-glucosyluronic acid residues and varying proportions of 0-acetyl and pyruvic acid acetal. The primary structure of xanthan gum is a cellulose backbone with trisaccharide side chains; the repeating unit is a pentasaccharide. Generally, the molecular weight is greater than about $10^6$ g/mole.

In some embodiments, L-lactic acid is a buffering agent that acts to maintain the pH of the vagina within its normal acidic range (i.e., a pH of less than about 5 and more preferably in the range of about 3.5 to about 4.5). In some embodiments, the composition further comprises a buffer. Non-limiting examples of buffering agents include, but are not limited to, citric acid, potassium acid tartrate, benzoic acid, alginic acid, sorbic acid, fumaric acid, ascorbic acid, stearic acid, oleic acid, tartaric acid, edetic acid ethylenediaminetetracetic acid, acetic acid, malic acid, and the like. In some instances, the acids are added as free acids, hydrates, or pharmaceutically acceptable salts. In some instances, the free acids are converted to the corresponding salts in situ (i.e., within the vagina). In some embodiments, several buffering agents are included in the combination gel to provide increased buffering capacity. In some embodiments, alginic acid, functions as both a polymer thickener and a buffering agent. In some instances, alginic acid is not absorbed by the body, thereby having a longer lasting acid buffering effect compared to the other buffering agents that are absorbed by the body.

In some instances, the compositions of the present disclosure include additional excipients. In some instances, the additional excipients include humectants. Suitable humectants include, but are not limited to, for example, glycerol, polyethylene glycols, propylene glycols, sorbitol, triacetin, and the like. In some embodiments, glycerol is used as a humectant to prevent the formation of a dry film on the gel when placed within the vagina. In certain embodiments, glycerol also acts as a lubricant. Additionally, the combination gel, in some embodiments, also includes a preservative. Suitable preservatives include, but are not limited to, for example, benzoic acid, sodium benzoate, methylparaben, ethylparaben, butylparaben, propylparaben, benzyalkonium chloride, phenylmercuric nitrate, chlorhexidine, and the like. In some embodiments, the preservative is benzoic acid. In some embodiments, the combination gel comprises benzoic acid, which is a preservative and also contributes to the buffering capacity of the combination gel.

In some embodiments, the composition further comprises one or more cosmetic ingredients. Such cosmetic ingredients include diluents, solvents, and adjuvants, for example; water, ethyl alcohol, isopropyl alcohol, glycerin, glycerol propylene glycol, sorbitol, and other high molecular weight alcohols. In addition, the composition, in certain embodiments, further comprises minor amounts of other additives, such as, for example; stabilizers, surfactants, menthol, eucalyptus oil, other essential oils, fragrances, and the like. The selection and amounts of cosmetic ingredients, other additives, and blending procedures are carried out in accordance with techniques well-known in the art.

In some embodiments, the pharmaceutical carrier is water. In some embodiments, the pharmaceutical carrier is aqueous based. Other pharmaceutically acceptable carriers that are suitable for vaginal delivery are well known and are used, in some examples, in place of water. One example of a suitable pharmaceutically acceptable carrier is petrolatum, such as white petrolatum.

In one exemplary embodiment of the present disclosure, the composition is further described as follows: the polymer thickener is alginic acid and xanthan gum; the preservative is benzoic acid; the humectant is glycerol; citric acid, potassium bitartrate, and L-lactic acid are acidic components; and water is the pharmaceutically acceptable carrier. In another embodiment, the composition contains xanthan gum, alginic acid, L-lactic acid, citric acid, benzoic acid, potassium bitartrate, glycerol, and water.

As discussed, L-lactic acid or other suitable buffering agents are used to maintain the pH of the vagina within its normal acidic range (i.e., a pH of less than about 5 and more preferably in the range of about 3.5 to about 4.5). Lactic acid has two isomers, one is known as L-(+)-lactic acid or (S)-lactic acid and the other is D-(−)-lactic acid or (R)-lactic acid. Recent discovery has shown that the L form of lactic acid is more potent in inactivating HIV than D or racemic lactic acid. It is contemplated herein that the L form of lactic acid is more potent in inactivating HIV than D or racemic lactic acid. While the precise mechanism of how L-lactic acid inactivates HIV is unknown, the stereochemical dependent activity suggests that it acts on proteins. Accordingly, the composition used in the methods described herein comprises L-lactic acid and provides an improved therapeutic effect compared to a similar composition comprising D-lactic acid.

The composition of the present disclosure is in the form of a gel, a semi-solid, a cream, a lotion, and/or a liquid. In some embodiments, the composition is injected. In some embodiments, the composition is instilled. In some embodiments, the composition is administered as a topical ointment applied to the lining of the vagina and/or cervix and/or rectum. In some instances, this is accomplished as a gel, cream, lotion, non-aqueous or aqueous solution used to flush the vaginal or rectal cavity, and/or a vaginal or rectal suppository. In other embodiments, the composition is administered in a spray formulation.

In some embodiments, the compositions of the present disclosure are delivered to the vagina of a mammal by any means known to those skilled in the art. Typical forms for delivery of the compositions include, for example; creams, lotions, gels, foams, intravaginal devices such as sponges and suppositories, and films. In some instances, the composition is additionally used as personal care products, such as, for example, condom lubricants, and the like. In some instances, such lubricants comprise commonly known ingredients such as, for example: humectants, e.g., glycerin, sorbitol, mannitol, glycols and glycol ethers; buffers, e.g., glucono-d-lactone; germicides or bactericides, e.g., chlorhexidine gluconate; preservatives, e.g., methylparaben; viscosifiers, e.g., hydroxyethyl cellulose, etc.; other adjuvants, e.g., colors and fragrances; in addition to the compositions of the present disclosure. Those skilled in the art will recognize that the physical properties, e.g., viscosity, of such delivery forms may vary widely. For example, in some instances, the viscosity of a gel form of the composition of the present disclosure, e.g., 150,000 centipoise, is substantially higher than the viscosity of lotion form of the composition of the present disclosure, e.g., 100 centipoise. Further details concerning the materials, ingredients, proportions and procedures of such delivery forms are selected in accordance with techniques known in the field.

In some embodiments, the composition described herein is intravaginally administered one or more times during a course of treatment. In some embodiments, the composition described herein is intravaginally administered once during a course of treatment. In some embodiments, the course of treatment is about 1 week to about 20 weeks. In some embodiments, the course of treatment is about 2 weeks to about 19 weeks. In some embodiments, the course of treatment is about 3 weeks to about 18 weeks. In some embodiments, the course of treatment is about 4 weeks to about 17 weeks. In some embodiments, the course of treatment is about 5 weeks to about 16 weeks. In some embodiments, the course of treatment is about 6 weeks to about 15 weeks. In some embodiments, the course of treatment is about 7 weeks to about 14 weeks. In some embodiments, the course of treatment is about 8 weeks to about 13 weeks. In some embodiments, the course of treatment is about 9 weeks to about 12 weeks. In some embodiments, the course of treatment is about 10 weeks to about 11 weeks. In certain embodiments, the course of treatment is about 3 weeks to about 16 weeks. In some embodiments, the course of treatment is about 1 week, about 2 weeks, about 3 weeks, about 4 weeks, about 5 weeks, about 6 weeks, about 7 weeks, about 8 weeks, about 9 weeks, about 10 weeks about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 7 months, about 8 months, about 9 months, about 10 months, about 11 months, about 12 months, about 13 months, or from about 6 months to about 24 months.

In some embodiments, the composition is intravaginally administered during the course of treatment daily, every other day, once a week, once every 2 weeks, once every 3 weeks, once every 4 weeks, once every 5 weeks, once every 6 weeks, once every 7 weeks, once every 8 weeks, once every 9 weeks, once every 10 weeks, once every 11 weeks, once every 12 weeks, once every 13 weeks, once every 14 weeks, once every 15 weeks, once every 16 weeks, once every 17 weeks, once every 18 weeks, once every 19 weeks, or once every 20 weeks.

In some embodiments, the course of treatment comprises an initial course of treatment and a subsequent course of treatment. In some embodiments, the initial course of treatment is shorter than the subsequent course of treatment. In some embodiments, the initial course of treatment is about 1 week to about 19 weeks. In some embodiments, the initial course of treatment is about 2 weeks to about 18 weeks. In some embodiments, the initial course of treatment is about 3 weeks to about 17 weeks. In some embodiments, the initial course of treatment is about 4 weeks to about 16 weeks. In some embodiments, the initial course of treatment is about 5 weeks to about 15 weeks. In some embodiments, the initial course of treatment is about 6 weeks to about 14 weeks. In some embodiments, the initial course of treatment is about 7 weeks to about 13 weeks. In some embodiments, the initial course of treatment is about 8 weeks to about 12 weeks. In some embodiments, the initial course of treatment is about 9 weeks to about 11 weeks. In some embodiments, the initial course of treatment is about 10 weeks to about 11 weeks. In some embodiments, the initial course of treatment is about 1 week to about 4 weeks. In some embodiments, the initial course of treatment is about 2 weeks to about 3 weeks. In some embodiments, the initial course of treatment is about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 7 months, about 8 months, about 9 months, about 10 months, about 11 months, about 12 months, about 13 months, or from about 6 months to about 24 months. In some embodiments, the subsequent course of treatment is about 1 week to about 19 weeks. In some embodiments, the subsequent course of treatment is about 2 week to about 18 weeks. In some embodiments, the subsequent course of treatment is about 3 weeks to about 17 weeks. In some embodiments, the subsequent course of treatment is about 4 weeks to about 16 weeks. In some embodiments, the subsequent course of treatment is about 5 weeks to about 15 weeks. In some embodiments, the subsequent course of treatment is about 6 weeks to about 14 weeks. In some embodiments, the subsequent course of treatment is about 7 weeks to about 13 weeks. In some embodiments, the subsequent course of treatment is about 8 weeks to about 12 weeks. In some embodiments, the subsequent course of treatment is about 9 weeks to about 10 weeks. In some embodiments, the subsequent course of treatment is about 10 weeks to about 11 weeks. In some embodiments, the subsequent course of treatment is about 1 week to about 4 weeks. In certain examples, the subsequent course of treatment is about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 7 months, about 8 months, about 9 months, about 10 months, about 11 months, about 12 months, about 13 months, or from about 6 months to about 24 months.

In embodiments wherein the course of treatment comprises an initial and a subsequent course of treatment, the frequency of intravaginal administration of the composition is different between the initial and the subsequent course of treatment. In some embodiments, the composition is intravaginally administered more frequently during the initial course of treatment than during the subsequent course of treatment. In some embodiments, the composition is intravaginally administered less frequently during the initial course of treatment than during the subsequent course of treatment.

In some embodiments, the composition is intravaginally administered during the initial course of treatment daily, every other day, once a week, once every 2 weeks, once every 3 weeks, once every 4 weeks, once every 5 weeks, once every 6 weeks, once every 7 weeks, once every 8 weeks, once every 9 weeks, once every 10 weeks, once every 11 weeks, once every 12 weeks, once every 13 weeks, once every 14 weeks, once every 15 weeks, once every 16 weeks, once every 17 weeks, once every 18 weeks, or once every 19 weeks. In some embodiments, the frequency of administration during the initial course is once a day, once every 12 hours, once every 6 hours, once every 4 hours, or once every 2 hours. In some embodiments, the frequency of administration during the initial course is such that there is no more than 24 hours gap between administration of two doses. In some embodiments, the frequency of administration during the initial course is such that there is no more than 48 hours gap between administration of two doses. In some embodiments, the frequency of administration during the initial course is such that there is no more than 72 hours gap between administration of two doses. In some embodiments, the frequency of administration during the initial course is such that there is no more than 96 hours gap between administration of two doses. In some embodiments, the frequency of administration during the initial course is such that there is no more than 120 hours gap between administration of two doses. In some embodiments, the frequency of administration during the initial course is such that there is no more than 168 hours gap between administration of two doses. In other embodiments, the frequency of administration during the initial course is such that there is more than 24 hours gap between administration of two doses. In other embodiments, the frequency of administration during the initial course is such that there is more than 48 hours gap between administration of two doses. In other embodiments, the frequency of administration during the initial course is such that there is more than 72 hours gap between administration of two doses. In other embodiments, the frequency of administration during the initial course is such that there is more than 96 hours gap between administration of two doses. In other embodiments, the frequency of administration during the initial course is such that there is more than 120 hours gap between administration of two doses. In other embodiments, the frequency of administration during the initial course is such that there is more than 168 hours gap between administration of two doses. In some cases, the initial course of treatment comprises about 1 week and the frequency of administration is once daily. In some cases, the initial course of treatment comprises about 1 week and the frequency of administration is such that there is more than 24 hours gap between administration of two doses. In some cases, the initial course of treatment comprises about 1 week and the frequency of administration is such that there is more than 48 hours gap between administration of two doses. In some cases, the initial course of treatment comprises about 1 week and the frequency of administration is such that there is more than 72 hours gap between administration of two doses. In some cases, the initial course of treatment comprises about 1 week and the frequency of administration is such that there is more than 96 hours gap between administration of two doses. In some cases, the initial course of treatment comprises about 1 week and the frequency of administration is such that there is more than 120 hours gap between administration of two doses. In some cases, the initial course of treatment comprises about 1 week and the frequency of administration is such that there is no more than 168 hours gap between administration of two doses. In some cases, the initial course of treatment comprises about 1 week and the frequency of administration is such that one dose is administered during the week. In some examples, the initial course of treatment comprises about 2 weeks and the frequency of administration is such that one dose is administered during the 2 weeks. In some cases, the initial course of treatment comprises about 2 weeks and the frequency of administration is such that at least two doses are administered during the 2 weeks. In some cases, the initial course of treatment comprises about 3 weeks and the frequency of administration is such that only one dose is administered during the three weeks.

In some embodiments, the composition is intravaginally administered during the subsequent course of treatment daily, every other day, once a week, once every 2 weeks, once every 3 weeks, once every 4 weeks, once every 5 weeks, once every 6 weeks, once every 7 weeks, once every 8 weeks, once every 9 weeks, once every 10 weeks, once every 11 weeks, once every 12 weeks, once every 13 weeks, once every 14 weeks, once every 15 weeks, once every 16 weeks, once every 17 weeks, once every 18 weeks, or once every 19 weeks. In some embodiments, the frequency of administration during the subsequent course is every other day, once a week, or twice a week. In some cases, the subsequent course of treatment comprises about 1 week and the frequency of administration is less than once daily. In some embodiments, the frequency of administration during the subsequent course is such that there is more than 24 hours gap between administration of two doses. In some embodiments, the frequency of administration during the subsequent course is such that there is more than 48 hours gap between administration of two doses. In some embodiments, the frequency of administration during the subsequent course is such that there is more than 72 hours gap between administration of two doses. In some embodiments, the frequency of administration during the subsequent course is such that there is more than 96 hours gap between administration of two doses. In some embodiments, the frequency of administration during the subsequent course is such that there is more than 120 hours gap between administration of two doses. In some embodiments, the frequency of administration during the subsequent course is such that there is more than 168 hours gap between administration of two doses. In some cases, the subsequent course of treatment comprises about 1 week and the frequency of administration is less than once daily. In some cases, the subsequent course of treatment comprises about 1 week and the frequency of administration is such that there is more than 24 hours gap between administration of two doses. In some cases, the subsequent course of treatment comprises about 1 week and the frequency of administration is such that there is more than 48 hours gap between administration of two doses. In some cases, the subsequent course of treatment comprises about 1 week and the frequency of administration is such that there is more than 72 hours gap between administration of two doses. In some cases, the subsequent course of treatment comprises about 1 week and the frequency of administration is such that there is more than 96 hours gap between administration of two doses. In some cases, the subsequent course of treatment comprises about 1 week and the frequency of administration is such that there is more than 120 hours gap between administration of two doses. In some cases, the subsequent course of treatment comprises about 1 week and the frequency of administration is such that there is no more than 168 hours gap between administration of two doses. In some cases, the subsequent course of treatment comprises about 1 week and the frequency of administration is such that one dose is administered during the week. In some examples, the subsequent course of treatment comprises about 2 weeks and the frequency of administration is such that one dose is administered during the 2 weeks. In some cases, the subsequent course of treatment comprises about 2 weeks and the frequency of administration is such that at least two doses are administered during the 2 weeks. In some cases, the subsequent course of treatment comprises about 3 weeks and the frequency of administration is such that only one dose is administered during the three weeks.

In some embodiments, administration of the composition described herein using methods described herein results in lowering of vaginal pH. In some embodiments, lowering of vaginal pH is observed after the first administration of the composition during a course of treatment. In some embodiments, lowering of vaginal pH is observed after at least two administrations of the composition during a course of treatment. In some embodiments, lowering of vaginal pH is observed after multiple administrations of the composition during a course of treatment. In some embodiments, lowering of vaginal pH is observed after the initial course of treatment. In some embodiments, lowering of vaginal pH is observed after the subsequent course of treatment. In some instances, administration of the composition lowers the vaginal pH by at least 0.1 compared to the baseline vaginal pH prior to the administration of the composition. In some instances, administration of the composition lowers the vaginal pH by at least 0.2 compared to the baseline vaginal pH prior to the administration of the composition. In some instances, administration of the composition lowers the vaginal pH by at least 0.3 compared to the baseline vaginal pH prior to the administration of the composition. In some instances, administration of the composition lowers the vaginal pH by at least 0.4 compared to the baseline vaginal pH prior to the administration of the composition. In some instances, administration of the composition lowers the vaginal pH by at least 0.5 compared to the baseline vaginal pH prior to the administration of the composition. In some instances, administration of the composition lowers the vaginal pH by at least 0.6 compared to the baseline vaginal pH prior to the administration of the composition. In some instances, administration of the composition lowers the vaginal pH by at least 0.7 compared to the baseline vaginal pH prior to the administration of the composition. In some instances, administration of the composition lowers the vaginal pH by at least 0.8 compared to the baseline vaginal pH prior to the administration of the composition. In some instances, administration of the composition lowers the vaginal pH by at least 0.9 compared to the baseline vaginal pH prior to the administration of the composition. In some instances, administration of the composition lowers the vaginal pH by at least 1.0 compared to the baseline vaginal pH prior to the administration of the composition. In some instances, administration of the composition lowers the vaginal pH by about 0.1 compared to the baseline vaginal pH prior to the administration of the composition. In some instances, administration of the composition lowers the vaginal pH by about 0.2 compared to the baseline vaginal pH prior to the administration of the composition. In some instances, administration of the composition lowers the vaginal pH by about 0.3 compared to the baseline vaginal pH prior to the administration of the composition. In some instances, administration of the composition lowers the vaginal pH by about 0.4 compared to the baseline vaginal pH prior to the administration of the composition. In some instances, administration of the composition lowers the vaginal pH by about 0.5 compared to the baseline vaginal pH prior to the administration of the composition. In some instances, administration of the composition lowers the vaginal pH by about 0.6 compared to the baseline vaginal pH prior to the administration of the composition. In some instances, administration of the composition lowers the vaginal pH by about 0.7 compared to the baseline vaginal pH prior to the administration of the composition. In some instances, administration of the composition lowers the vaginal pH by about 0.8 compared to the baseline vaginal pH prior to the administration of the composition. In some instances, administration of the composition lowers the vaginal pH by about 0.9 compared to the baseline vaginal pH prior to the administration of the composition. In some instances, administration of the composition lowers the vaginal pH by about 1.0 compared to the baseline vaginal pH prior to the administration of the composition.

In some embodiments, administration of the composition described herein using methods described herein restores a healthy vaginal microbiome. In some embodiments, restoration of a healthy vaginal microbiome is characterized by an increase in population of aerobic microbes and a decrease in population of anaerobic microbes, such as *Gardnerella vaginalis, Prevotella, Peptostreptococcus*, and *Bacteroides* spp. In some embodiments, a healthy vaginal microbiome is restored after the first administration of the composition during a course of treatment. In some embodiments, a healthy vaginal microbiome is restored after at least two administrations of the composition during a course of treatment. In some embodiments, a healthy vaginal microbiome is restored after the initial course of treatment. In some embodiments, a healthy vaginal microbiome is restored after the subsequent course of treatment.

In some embodiments, the compositions of the present disclosure are administered to the vagina of the mammal in a dosage comprising about 0.5 g to about 10 g, about 2 g to about 9 g, about 3 g to about 8 g, about 4 g to about 7 g, about 5 g to about 6 g, about between 3 g to about 4 g, or about 4 g to about 5 g of the composition. The dosage of administration, in some embodiments comprises about 0.5 g, about 0.6 g, about 0.7 g, about 0.8 g, about 0.9 g, about 1 g, about 1.1 g, about 1.2 g, about 1.3 g, about 1.4 g, about 1.5 g, about 1.6 g, about 1.7 g, about 1.8 g, about 1.9 g, about 2 g, about 2.1 g, about 2.2 g, about 2.3 g, about 2.4 g, about 2.5 g, about 2.6 g, about 2.7 g, about 2.8 g, about 2.9 g, about 3 g, about 3.1 g, about 3.2 g, about 3.3 g, about 3.4 g, about 3.5, about 3.6 g, about 3.7 g, about 3.8, about 3.9, about 4 g, about 5 g, about 5.1 g, about 5.2 g, about 5.3 g, about 5.4 g, about 5.5 g, about 5.6 g, about 5.7 g, about 5.8 g, about 5.9 g, about 6 g, about 7 g, about 7.1 g, about 7.2 g, about 7.3 g, about 7.4 g, about 7.5 g, about 7.6 g, about 7.7 g, about 7.8, about 7.9 g, about 8 g, about 8.1 g, about 8.2 g, about 8.3 g, about 8.4 g, about 8.5 g, about 8.6 g, about 8.7 g, about 8.8 g, about 8.9 g, about 9 g, about 9.1 g, about 9.2 g, about 9.3, about 9.4 g, about 9.5 g, about 9.6 g, about 9.7, about 9.8 g, about 9.9 g, about 10 g, about 10.1 g, about 10.2 g, about 10.3 g, about 10.4 g, about 10.5 g, about 10.6 g, about 10.7 g, about 10.8 g, about 10.9 g, about 11 g, about 11.1 g, about 11.2 g, about 11.3 g, about 11.4 g, about 11.5 g, about 11.6 g, about 11.7 g, about 11.8 g, about 11.9 g, about 12 g, about 12.1 g, about 12.2 g, about 12.3 g, about 12.4 g, about 12.5 g, about 12.6 g, about 12.7 g, about 12.8 g, about 12.9 g, about 13 g, about 13.1 g, about 13.2 g, about 13.3 g, about 13.4 g, about 13.5 g, about 13.6 g, about 13.7 g, about 13.8 g, about 13.9 g, about 14 g, about 14.1 g, about 14.2 g, about 14.3 g, about 14.4 g, about 14.5 g, about 14.6 g, about 14.7 g, about 14.8 g, about 14.9 g, about 15 g, about 15.1 g, about 15.2 g, about 15.3 g, about 15.4 g, about 15.5 g, about 15.6 g, about 15.7 g, about 15.8 g, about 15.9 g, about 16 g, 16.1 g, about 16.2 g, about 16.3 g, about 16.4 g, about 16.5 g, about 16.6 g, about 16.7 g, about 16.8 g, about 16.9 g, about 17 g, about 17.1 g, about 17.2 g, about 17.3 g, about 17.4 g, about 17.5 g, about 17.6 g, about 17.7 g, about 17.8 g, about 17.9 g, about 18 g, about 18.1 g, about 18.2 g, about 18.3 g, about 18.4 g, about 18.5 g, about 18.6 g, about 18.7 g, about 18.8 g, about 18.9 g, about 19 g, about 19.1 g, about 19.2 g, about 19.3 g, about 19.4 g, about 19.5 g, about 19.6 g, about 19.7 g, about 19.8 g, about 19.9 g, or about 20 g of the composition.

The present disclosure further provides a method for prognosis of risk of recurrence of BV, the method comprising assessment of BV in a subject by testing vaginal pH, administration of the composition described herein according to the methods described herein, followed by re-assessment of BV in the subject by re-testing vaginal pH, and prognosing the risk of recurrence of BV based of comparisons of vaginal pH before and after administration of the composition. In some embodiments, the vaginal pH is lowered after administration of the composition described herein according to methods described above. In some embodiments, lowering of vaginal pH in a subject following administration of the composition described herein according to the methods described herein is associated with good prognosis for reduced risk of recurrence of BV in the subject.

Another embodiment provides a method for prognosis of risk of recurrence of BV, the method comprising assessment of BV in a subject by a first vaginal microbiome analysis, administration of the composition described herein according to the methods described herein, followed by re-assessment of BV in the subject by a subsequent vaginal microbiome analysis, and prognosing the risk of recurrence of BV based of comparisons of vaginal microbiome analysis before and after administration of the composition. In some embodiments, administration of the composition described herein according to methods described above, restores a healthy vaginal microbiome in a subject. In some embodiments, restoration of a healthy vaginal microbiome is characterized by an increase in population of aerobic microbes, such as *Lactobacillus* spp. and a decrease in population of anaerobic microbes, such as *Gardnerella vaginalis, Prevotella, Peptostreptococcus*, and *Bacteroides* spp. In some embodiments, restoration of a healthy vaginal microbiome in a subject following administration of the composition described herein according to the methods described herein is associated with good prognosis for reduced risk of recurrence of BV in the subject.

A further embodiment provides a method of prognosis of risk of recurrence of BV, the method comprising assessment of BV in a subject using Amsel criteria, administration of the composition described herein according to the methods described herein, followed by re-assessment of BV in the subject using Amsel criteria, and prognosing the risk of recurrence of BV based of comparisons of Amsel criteria results before and after administration of the composition. In some embodiments, following intravaginal administration of the composition the subject does not meet at least three of four Amsel criteria. The subject is then defined as Amsel-negative. In some embodiments, the subject is Amsel-negative after a first intravaginal administration of the composition during a course of treatment. In some embodiments, the subject is Amsel-negative after at least two intravaginal administrations of the composition during a course of treatment. In some embodiments, the subject is Amsel-negative after the initial course of treatment. In some embodiments, the subject is Amsel-negative after the subsequent course of treatment. In some embodiments, an Amsel-negative subject is considered to have a good prognosis for reduced risk of recurrence of BV in the subject. In some embodiments, an Amsel-positive subject is considered to have a poor prognosis for reduced risk of recurrence of BV in the subject.

EXAMPLES

The following specific, non-limiting examples are to be construed as merely illustrative, and do not limit the present disclosure of the scope of the disclosure. Without further elaboration, it is believed that one skilled in the art can, based on the description herein, utilize the present disclosure to its fullest extent.

Example 1: A Randomized, Placebo Controlled Pilot Study to Determine the Effect and Duration of One Exemplary Gel Formulation (e.g., Acidform or Amphora® Gel) on Vaginal pH A total of 100 female subjects, aged 18 to 45 years, will be enrolled for the study. The study will be carried out in two sites with 50 subjects for each site. It is anticipated there will be approximately 26 weeks, including a three month period to complete enrollment, between study activation and the final monitoring close-out visit. The enrolled subjects will participate in the study according to the following schedule: Screening, Day 0; Admission/Dosing/Monitoring, Day 1; Discharge, Day 2; Self-obtained vaginal pH readings, Days 2-6; Outpatient clinic visit, Day 7.

An intravaginally (IVAG) applied exemplary gel formulation (e.g., Acidform or Amphora® Gel) will be used as the investigational product (IP) in the study. The exemplary gel formulation (e.g., Acidform or Amphora® Gel) is an acidity-maintaining gel (pH 3.5) containing three acidic compounds (citric acid, potassium bitartrate, and lactic acid), a preservative (benzoic acid), two natural polymer thickeners (alginic acid and xanthan gum), a humectant (glycerin), and water. The exemplary gel formulation (e.g., Acidform or Amphora® Gel) will be administered at a dosage of 3, 4, or 5 g, IVAG.

Universal Placebo Gel (UPG), an isotonic non-buffering gel, pH adjusted to 4.5, containing 2.7% hydroxyethylcellulose, sorbic acid, sodium hydroxide, sodium chloride and purified water, will be used as a control. UPG will be administered at a dosage of 4 g, IVAG.

Primary Objective of the study is to determine effect and duration of one IVAG dose (3, 4 or 5 g) of the exemplary gel formulation (e.g., Acidform or Amphora® Gel) or placebo gel (4 g UPG) or no treatment, on vaginal pH in women. Exploratory objectives of the study are: (1) To determine the effect of one IVAG dose of the exemplary gel formulation (e.g., Acidform or Amphora® Gel) at a dose of 3, 4 or 5 g, or placebo gel (4 g UPG) or no treatment, on asymptomatic bacterial vaginosis (BV) based on Amsel criteria., (2) To determine the effect of a single application of the exemplary gel formulation (e.g., Acidform or Amphora® Gel) at a dose of 3, 4 or 5 g on the vaginal microbiome.

Primary Outcome measures of the study is to assess change in vaginal pH and duration of change from baseline pH following a single dose (3, 4 or 5 g) of IVAG the exemplary gel formulation (e.g., Acidform or Amphora® Gel), placebo gel (4 g UPG), or no treatment. Exploratory outcome measures: (1) To determine the effect of a single dose (3, 4 or 5 g) of IVAG the exemplary gel formulation (e.g., Acidform or Amphora® Gel), placebo gel (4 g UPG) or no treatment on asymptomatic BV based on Amsel's criteria, (2) To determine the effect of a single application of the exemplary gel formulation (e.g., Acidform or Amphora® Gel) at a dose of 3, 4 or 5 g on the vaginal microbiome.

Study Participants: One hundred volunteer women, 20 per each treatment arm, will be treated with either IVAG the exemplary gel formulation (e.g., Acidform or Amphora® Gel), 5 g dose (GROUP A); 4 g dose (GROUP B); 3 g dose (GROUP C); or Universal Placebo Gel (UPG), 4 g (GROUP D); or no treatment (GROUP E). For GROUPS A, B, C and D, treatment is defined as speculum exam plus instillation of Investigational Product (IP) or placebo gel. For GROUP E (control), treatment is defined as speculum exam and no gel instillation. At least 13 women in each group will be of either African American or Hispanic ethnicity.

Study Protocol: Routine screening tests will be performed on admission; and subjects will be assessed for asymptomatic BV via vaginal swabs obtained for grading by Amsel criteria. A direct vaginal pH reading will be research staff-obtained before the speculum exam, as well as one hour, and six hours post-treatment (Day 0). At the one hour and six hours post treatment time points, direct vaginal pH readings will be taken on specimens collected from two different positions in the vagina, in case of incomplete distribution of the IP immediately following instillation. Both readings will be included as data points. At the six hours time point, subjects will be trained on self-collecting vaginal swabs and performing the vaginal pH test. At 12 hours post-treatment, subjects will perform the vaginal pH test themselves using self-obtained swabs, and record their results for clinician review. Clinicians will collect AE assessment data will at each post treatment vaginal pH testing time point while subjects are in the domiciliary unit (1, 6, 12, and 24 hours post-treatment).

The vaginal microbiome collection will be done on the women who consent for this. The same swab used for vaginal pH at the Baseline/Screening will be used for the microbiome analysis post 24 hours treatment and on days 2 through 7. The research staff will obtain the Baseline/Screening (a repeat pH/microbiome swab will be taken if screening and admission to the domiciliary unit does not take place on the same day), post 24 hour treatment and day 7 readings. The subjects will obtain the microbiome readings on days 2-6 at home, concurrently with the pH readings.

Subjects will stay overnight in the domiciliary unit of the clinical trial center, and vaginal pH, microbiome collection (consented subjects) and Amsel criteria will be measured again by research staff at 24 (+/−2) hours post-treatment before discharge on Day 1. The subjects will be discharged with the appropriate pH testing supplies and diary. All women must agree to abstain from sexual intercourse, douching and use of any intravaginally applied products or devices until after their final study visit on Day 7. Subjects will measure their vaginal pH and do the microbiome collection (if consented) at 24 (+/−4) hour intervals for 5 days (Days 2-6) as outpatients and record the pH test results, any change in vaginal comfort, and confirmation of microbiome swab saved (for consented subjects) in a provided diary. Subjects will also record any activities engaged in from the abstinence criteria in the study exclusion list, if applicable, each day. On Day 7 (+/−24 hours), subjects will return to the clinic with their diaries, swab transport containers, have their vaginal pH and Amsel criteria determined by the clinic staff, and queried as to any vaginal discomfort (vaginal comfort assessment) over the course of the study, as self-recorded in their diaries.

Screening and Eligibility: Screening, eligibility assessment and enrollment may all occur on the same day. Admission to the domiciliary unit for dosing and 24 hour observation may also occur on the same day as the Screening visit.

However, enrolled subjects who are unable to be admitted for day activities on the same day as screening may be admitted up to 5 days post screening, provided the following: (1) Subjects who are not admitted on the same day as screening, but within 48 hours of screening, have a urine pregnancy (UHCG) and vaginal pH test, medical/surgical history, concomitant medications, and vital signs repeated upon admission. If subject has consented to microbiome collection, the swab will again be collected, (2) Subjects admitted more than 48 hours but up to 5 days post Screening have a urine pregnancy (UHCG), vaginal pH test, speculum exam, vaginal smear for Amsel criteria, medical/surgical history, concomitant medications, and vital signs repeated upon admittance. If subject consents to microbiome collection, the swab will again be collected.

Intervention and Follow-up Period: The Intervention and Follow-up Period is Day 0-Day 7 in the Schedule of Events (Appendix A). The protocol defined period of observation is 8 days.

Safety Follow-up After Protocol Defined Period of Observation: This period includes safety follow-up as required by Good Clinical Practice and standard clinical trial practice. Adverse events continuing after Day 7 (Final Study Visit) will be followed until resolution or stable status as determined by the principal investigator at the clinical trial site.

Study Outcome Measures:

Primary Outcome Measures will include assessment of change in vaginal pH from baseline, post-instillation of one dose of IVAG the exemplary gel formulation (e.g., Acidform or Amphora® Gel), placebo gel, or no treatment; as well as duration of this change in vaginal pH.

Exploratory Outcome Measures will include assessment of effect of a single dose of IVAG the exemplary gel formulation (e.g., Acidform or Amphora® Gel) gel, placebo gel or no treatment on asymptomatic BV, based on Amsel criteria.

Study Population: Approximately 150 women will be screened to identify 100 female subjects who are eligible to participate. Up to fifteen additional subjects will be selected to account for subjects who are lost to follow up or who are withdrawn.

Schedule for individual subjects: Individual subjects will participate in the study for approximately eight days. The study schedule to be followed is shown in FIG. 1 and also described below in details.

Study Enrollment and Retention: No study procedures will be performed until informed consent is obtained as part of the enrollment process. One hundred female subjects, ages 18-45, will be enrolled. Subjects will be recruited through IRB-approved advertisements, database queries, and word of mouth. Children, pregnant women, prisoners, and other vulnerable populations will not be enrolled. Because vaginal pH values have been found to vary by ethnicity, recruitment efforts will focus on enrollment of at least 65 women of African American or Hispanic descent (ideally, nearly equal numbers of each race at each site).

Screening will begin with the principal investigator at the clinical triat site or a designee providing an overview of the study to the potential subject. Subjects will be excluded if they do not understand the protocol and participation requirements and/or if they are unlikely or unwilling to remain in the domiciliary unit overnight, conduct vaginal pH readings on self-obtained vaginal swabs at home, or attend the Day 7 follow-up visit. Potential subjects will be invited to the study-designated clinic area for additional screening procedures and information about the study. Potential subject will be assigned a screening number. Study retention strategies will include clear explanations during enrollment of the study schedule and procedures and reimbursement to support travel and time spent in clinic. Subjects will be reminded of visits beforehand, and study staff will contact those who miss appointments.

Eligibility Criteria: All eligibility criteria must be met for inclusion into the study; no waivers will be granted.

Inclusion Criteria:

1. Female subjects between 18 and 45 years, inclusive
2. Ability to understand the consent process and procedures 3. Subjects agree to be available for all study visits
4. Written informed consent in accordance with institutional guidelines
5. Negative pregnancy test
6. Able and willing to comply with all study procedures
7. Have not engaged in sexual intercourse, douching or used of any form of vaginal suppository or intravaginal device for 24 hours prior to enrollment.
8. Agree to abstain from sexual intercourse, douching or any form of vaginal suppository or intravaginal device use during course of study
9. Report menstrual cycle regularity (25- to 35-day menstrual cycles)
10. Subjects who test negative for BV or are positive for BV, but asymptomatic. (BV positive subjects will be referred for treatment at or following the Day 7 follow-up visit)

Exclusion Criteria:
1. Participation in any study with an investigational compound or device within 30 days prior to signing informed consent
2. Active drug or alcohol use or dependence that, in the opinion of the investigator, would interfere with adherence to study protocol
3. Any other medical condition(s) that, in the judgment of the investigator, might interfere with the study or require treatment that might interfere with the study
4. Family member of the investigation study staff
5. Pregnant or breast-feeding
6. Inability to provide informed consent
7. A subject with a history or expectation of noncompliance with medications or treatment protocol
8. Women with symptoms of UTI, symptomatic BV, yeast infection or STI reported or observed during examination or based on laboratory testing performed. (Should the study clinician make a presumptive diagnosis of such infections, these subjects will be withdrawn, referred for standard of care treatment, but will not be followed as part of this study. They may be re-screened for potential enrollment 14 days after treatment per Section 6.3, Prohibited Medications, if all other screening criteria are met.)
9. Women who regularly use douches, vaginal medications or suppositories, feminine sprays, genital wipes or contraceptive spermicides, or report abnormal vaginal discharge in the past 48 hours prior to screening
10. Women who are menstruating or who would expect to menstruate during the study
11. Women who are currently using contraceptives that are directly delivered to the vaginal mucosa, such as NuvaRing
12. Any specific condition that, in the judgment of the Investigator, precludes participation because it could affect subject safety Prohibited Medications:

Subjects must not be currently taking or applying, or have taken or applied, for a period of 14 days prior to screening, any antibiotic, antimycotic, or probiotic compounds, oral or intravaginal.

Randomization: This is a Phase I randomized controlled trial, 20 subjects per treatment arm; for a total of 100 subjects. Up to 15 alternates may be enrolled to account for study subjects that drop out or are lost to follow-up. The 100 subjects will be randomized in a 1:1:1:1:1 fashion across the five study groups. Simple randomization will be performed and all documentation of this procedure and output will be saved with the study biostatistician's files until the end of the study. The randomization list will be generated by the study biostatistician and transferred to study pharmacist prior to start of the study. Randomization will occur following enrollment and prior to Day 0 procedures. Alternates will be screened and enrolled if randomized subjects do not meet inclusion criteria on Day 0.

Blinding:

Study subjects in Groups A, B, C and D will remain blinded to their treatment assignment (with the exemplary gel formulation (e.g., Acidform or Amphora® Gel) at 5 g, 4 g, 3 g, or placebo gel), during the entire duration of the study. The Sponsor, Evofem, Inc., will prepare IP as well as placebo, and supply these products in ready to dispense status.

Withdrawal and Reasons for Withdrawal: A study subject will be discontinued from participation in the study for:
Development of any Exclusion criteria;
Pregnancy or breastfeeding;
Request by subject to terminate participation;
Requirement for prohibited treatment (see Exclusion criteria) before Day 7
Treatment-related toxicity;
Failure to adhere to requirements of the protocol including treatment and safety monitoring;
Lost to follow-up;
Request of primary care provider;
At the request of the IRB/Ethics committee, FDA, or the Sponsor;
Incarceration;
The subject's well-being, based on the opinion of the clinical trial site principal investigator.

Handling of Withdrawal:

If a subject is withdrawn from participation, the reason(s) for discontinuation must be documented in the source documents and eCRFs. Subjects who withdraw or are withdrawn from the study who received any amount of the study product will be encouraged to return for a follow-up (with subjects' consent) visit for safety. The subject will be asked for consent to complete an end-of-study evaluation (all procedures from Final Study Visit, Day 7). If an AE or SAE has occurred, every effort will be made to undertake protocol-specified safety follow-up procedures, and the subject will be encouraged to receive appropriate care under medical supervision until the symptoms of any AE resolve or the subject's condition becomes stable.

Handling Lost to Follow-Up:

The study design has incorporated primary, secondary, and tertiary strategies for reducing lost to follow-up. Primary strategies include having sites: fully inform subjects of study visit details prior to randomization, addressing subjects' expectations on study participation, motivating subjects to adhere to follow-up visits and research protocols, tracking subjects with overdue visits and having an alternate subject contact on file. Secondary strategies include: scheduling the Final Study Visit (Day 7) around subjects availability which are within the visit window, providing a visit reminder ahead of time, and reviewing data for missed and overdue follow-up visits. Tertiary strategies include: discussing subjects' difficulty in adhering to study protocol and answering any question they might have, continuing attempts to reach lost to follow-up subject and recording all contact attempts. Documentation of lost to follow-up status will be maintained in the subject's CRF and in source documents. The reason(s) for the lost to follow-up, if known, and the appropriate timelines for subject-study site correspondence will be captured along with the study site's attempts to reach the subject. Lastly, all proper procedures of sending certified letter of discontinuation from study based on lost to follow-up status and a recommendation to come in for a discontinuation visit to determine safety of the subject will be followed by the study site.

Alternate Subject Enrollment to Account for Lost to Follow-Ups and Withdrawals:

If an enrolled subject is lost to follow-up or withdrawal as described in Section 6.6.3 at any point prior to and including Day 7 (Final Study Visit) the following procedure will apply. An alternate subject who is enrolled in the study to account for a subject who withdrew from the study, or was Lost to Follow-up, will be assigned from the alternates list, and randomized per the study's randomization procedures.

Termination of the Study:

The study may be terminated at the discretion of the Sponsor for concerns of subject safety or any other reason. The study may also be closed by the clinical trial sites with the agreement of the sponsor, the FDA, or as the result of a natural disaster.

Investigational product (IP): The IP, which is one exemplary gel formulation (e.g., Acidform or Amphora® Gel) is an acidity-maintaining gel (pH 3.5) containing three acidic compounds (citric acid, potassium bitartrate, and lactic acid), a preservative (benzoic acid), two natural polymer thickeners (alginic acid and xanthan gum), a humectant (glycerin), and water. Sodium hydroxide is used to adjust the pH during manufacture. The placebo used in this study is Universal Placebo Gel (UPG). UPG is an isotonic non-buffering gel, pH adjusted to 4.5, containing 2.7% hydroxyethylcellulose, sorbic acid, sodium hydroxide, sodium chloride and purified water. In clinical trials, UPG has been proven safe and acceptable when used up to twice daily for 14 days. Table 1 lists the ingredients of the exemplary formulation, IP, that was used in the clinical trial, for which results are provided in Example 2.

TABLE 1

Formulation Chart for IP

| Ingredient | % w/w |
| --- | --- |
| Benzoic Acid | 0.20 |
| 10N NaOH | 2.20 |
| Purified Water USP | 74.00 |
| Potassium Bitartrate | 0.40 |
| Citric Acid | 1.00 |
| Lactic Acid 90% Solution | 2.00 |
| Alginic Acid (Protacid F120) | 4.25 |
| Glycerin | 8.00 |
| Xanthan Gum (Vanzan NF-C) | 3.00 |
| 10N NaOH adjust to pH 3.5 | As needed |
| Purified Water USP | Qs to 100 |

Formulation, and Packaging of the IP:

For this study, single use applicators will be used. The IP and placebo gels will be filled into unit-dose applicators consisting of an injection molded opaque white polyethylene barrel with a rounded distal end for easy insertion. A thermoplastic rubber piston will be inserted at the opposite end of the barrel. This component will seal the end of the barrel to keep the contents stable over time and also functions as the applicator piston when in use. A polyethylene plunger rod will be packaged alongside of the barrel within a plastic film sanitary overwrap. The research study kit will contain a group of overwrapped applicators placed into a standard white cardboard box along with instructions for use.

Product Supply:

The IP, which is one exemplary gel formulation (e.g., Acidform or Amphora® Gel) and the UPG placebo will be obtained from the Sponsor.

Product Storage, Stability, and Expiration:

The filled applicators will be stored at room temperature (15° C.-30° C.). Applicators will be maintained in the research pharmacy and dispensed by the site Research Pharmacist.

Preparation:

The study product is supplied ready for use. No preparation will be necessary.

Administration: The study product will be administered (instilled) by the study clinician on Day 0, following subject admission to the domiciliary unit. Gel instillation occurs after the gynecologic exam; no speculum is used during administration. In use, the plunger rod will be inserted into the piston end of the barrel engaging the piston. The cap will be removed from the distal end of the barrel; the barrel will then be inserted into the subject's vagina (distal end first). The plunger rod will be pushed into the barrel, subsequently moving the piston and gel toward the open end of the barrel. Only the gel will leave the barrel. These are the instructions supplied to the research staff with the study product.

TABLE 2

Investigational Product Dosing

| Treatment Group | Investigational Product* | Placebo** |
| --- | --- | --- |
| Group A | 20 subjects, 5 g dose | N/A |
| Group B | 20 subjects, 4 g dose | N/A |
| Group C | 20 subjects, 3 g dose | N/A |
| Group D | N/A | 20 subjects, UPG, 4 g dose |
| Group E*** | N/A | N/A |

The dosage of IP is 5 g, 4 g or 3 g (as described for each treatment group) in a pre-filled applicator. Administered by clinician on Day 0 only The dosage of placebo (UPG) is 4 g in a pre-filled applicator. Administered by clinician on Day 0 only. Control group will receive no treatment.

Accountability/Final Disposition for the Investigational Product(s):

The clinical trial site principal investigator will keep a record of the dates and amounts of IP and placebo received, including packing slips, the amount dispensed to study subjects, and the amount unused. These records should include the dates, quantities, batch/serial numbers and expiration dates (if applicable).

The Site PI will record drug accountability on a Drug Disposition Log. All used applicators can be discarded per clinic policy (Appendix D). Upon completion of the study and the final drug accountability monitoring visit, all unused study medication will be returned to the sponsor or, if instructed by the sponsor, unused study product may be destroyed onsite according to the site Research Pharmacy procedures.

Detailed study procedures/evaluations: Subjects will undergo the following study procedures as indicated in this section. All equipment used will be calibrated and validated as appropriate.

Written Informed Consent:

A written Informed Consent will be obtained from all study participants before start of any study activities. The Informed Consent has been developed in accordance with the International Conference on Harmonization Good Clinical Practices (ICH-GCP) guidelines. The Informed Consent specifies, in lay and culturally appropriate language, all expectations from the participant including duration of study, number of doses and visits, procedures at each visit, safety documentation including subject diary, explanation of abstinence expectations, restrictions on intravaginal products or device use, sampling plan, potential risks, stipend for participation in study, and relevant research scope. All study-related questions by the subject should be responded to before completion of the Informed Consent. The subject will be provided ample time, privacy and any questions about the ICF will be addressed. The completed Informed Consent form will be verified for its proper completion including that all required initials and signatures are in place. A signed copy of the Informed Consent will be provided to the subject and the original will be kept on-file in the subject's study-file (documentation).

Inclusion/Exclusion Criteria:

Participants will meet all the stated inclusion criteria and not possess any of the exclusion criteria to be eligible to participate in this study. Only subjects that are eligible based on the trial's inclusion and exclusion criteria will be enrolled in the trial.

Evaluation of Eligibility Criteria:

The clinical trial site principal investigator will evaluate whether a subject meets the study's inclusion/exclusion criteria as mentioned in the Inclusion/Exclusion Criteria listed above, at screening and before administering any study product. The clinical trial site principal investigator will be responsible for ensuring that the evaluation of eligibility criteria is addressed for all subjects enrolled in the study.

Demographics:

Demographics data will be collected from all study participants. Subject's date of birth, race, and ethnicity will be collected and recorded as part of demographics data.

Clinical Evaluations:

Summarized procedural steps for these evaluations are provided for information only; all procedures will be performed according to site/clinic standard of care SOPs (standard operating procedures).

Medical History:

A detailed medical/surgical/gynecologic/sexual health history will be obtained by a trained study staff. Changes in medical history, if applicable, will be reviewed at follow-up visits. A review of body systems will be performed by the principal investigator at the clinical trial site (Site PI) to screen for exclusion criteria.

Vital Signs:

Vital signs, including blood pressure, heart rate, and body temperature will be measured and recorded. Vital sign measurements will be obtained after the subject has been sitting quietly for at least 5 minutes. When taking an oral temperature, assure the subject has not had any recent hot or cold beverages or smoking. The Site PI should use clinical judgment when characterizing bradycardia among health subjects, for example conditioned athletes.

Gynecologic Examinations:

A full gynecologic examination (speculum) will be performed by a licensed practitioner, after swabs for vaginal pH and microbiome collection (in consented subjects) are collected. Clinicians will follow clinic procedures for these examinations, which in general will be performed as follows:

1. Each step of the exam will be explained to the subject
2. The subject is asked to assume the lithotomy position
3. External genitalia are assessed for abnormalities; i.e, signs of infection or inflammation
4. The closed speculum is introduced at a downward 45° angle. Should lubrication be necessary, warm water (only) may be used to facilitate insertion of the speculum; use of water to lubricate is noted in the source documents. After the speculum has entered the vagina, the blades of the speculum are rotated into a horizontal position. After full insertion, the speculum blades are opened and maneuvered gently so that the cervix comes into full view. The cervical os and vaginal walls are visually inspected for presence of discharge, inflammation, or irritation A targeted physical and/or gynecologic examination (speculum), will be performed at any subsequent or unscheduled visit if necessary due to an adverse event (AE).

Concomitant Medications:

Concomitant medications will be assessed and includes any medication that would be taken during the study including all over the counter medications, vitamins and nutritional supplements. The information collected for each concomitant medication included at a minimum: start date, stop date or continuing and indication.

Height and Weight:

Body weight without coat and shoes and height without shoes will be recorded.

Laboratory Evaluations

Pregnancy Testing:

Women of reproductive potential including those with history of tubal ligation participating in the study will be required to collect a urine specimen to be tested for urine (3-human chorionic gonadotropin (UHCG). Negative results must be obtained prior to dosing. Pregnancy testing will not be required for women who have undergone a total hysterectomy with clinical proof of the procedure performed (should be >2 months before start of study). Women who test positive for pregnancy will be excluded from participating in this study and be referred for follow-up as per clinic protocol, not as part of this study.

HIV Testing:

All subjects will have blood drawn for a serum HIV test. Specimen collection and testing shall be performed in accordance with site laboratory SOPs. HIV testing is performed for post-hoc analysis; HIV status is not an inclusion/exclusion criteria, therefore enrollment of subjects will not be based on test results. Those subjects who test HIV positive will be referred for follow-up as per clinic protocol, not as part of this study. Subjects who have positive HIV laboratory results available in their medical record, will not need to be re-tested (those results need to be placed in the research source record).

Vaginal pH Testing (Procedural steps for performing the vaginal pH test will be supplied to research staff and subjects as a one page, step by step pictorial reference sheet): Swab for vaginal pH reading will be collected prior to introduction of speculum for gynecologic exam.

Following instructions will be given to the research stuff for specimen collection:

1. Remove one strip of pH paper from the container. Place on a sheet of plain white paper, in natural light.
2. Open swab (applicator) package, remove one swab, taking care not to touch tip of swab to environmental or body surfaces.

3. Collect vaginal material on a swab:
   a. Insert one swab into the vagina approximately 2-3 inches, and then rub the vaginal wall at this position in a circular motion for approximately 15 seconds.
   b. For sample collection while the subject is in the domiciliary unit, each sampling time point will have up to 3 swabs collected (baseline, post treatment 1, 6, 12 and 24 hours). This sample is obtained as follows: Insert one swab into the vagina and collect vaginal material from the apex by rubbing the vaginal wall at this position in a circular motion for approximately 15 seconds.
4. Microbiome collection in subjects who have consented:
   a. Replace one of the pH collection swabs with the Copan ESwab. Collect pH as above; following the placement of vaginal secretion onto the pH paper, place swab into transport medium container and store in freezer.

Following instructions will be given to the study participant for specimen collection:
1. Remove one strip of pH paper; Place on a sheet of plain white paper, in natural light.
2. Open swab (applicator) package, remove one swab, taking care not to touch tip of swab to environmental or body surfaces.
3. Collect vaginal material on a swab by inserting one swab approximately 2-3 inches into the vagina, and then rubbing the vaginal wall in a circular motion for approximately 15 seconds.
4. For subjects that consented to the microbiome collection: Place swab in transport medium container and store in freezer until return to clinic on Day 7.

Following instructions will be given to the research stuff and study participant for vaginal testing:
1. Remove swab from vagina and immediately, using a circular motion, gently apply the vaginal material on the swab over the surface of one strip of pH paper.
2. Immediately (within 30 seconds) observe the color reaction on the paper and compare the color to the manufacturer supplied color comparison chart.
3. Record the pH value corresponding to the color comparison example closest in color on the comparison chart.

Following instructions will be given for Wet Prep Testing as a step by step pictorial reference sheet:
1. Introduce speculum as described above in Gynecologic Examinations section.
2. Open cotton tipped applicator package, remove one swab, taking care not to touch tip of swab to environmental or body surfaces.
3. Collect vaginal material on a swab by inserting one swab approximately 2-3 inches into the vagina, and then rubbing the vaginal wall in a circular motion for approximately 15 seconds, or by collecting material from the posterior fornices. Note: If sufficient material is collected, both the wet prep and the whiff test can be performed on one swab.
4. Remove swab and place the collected material in a small test tube containing approximately 0.5 mL of 0.85% nonbacteriostatic normal saline (this sample can be used for both the whiff test and the wet mount examination if necessary)
5. Label the tube with subject identifier
6. Maintain the specimen at room temperature (do not refrigerate)
7. Apply one drop of collected material to a clean glass slide
8. Place a coverslip over the sample on the slide
9. Examine the slide at 10× and 40× objective for epithelial cells, clue cells, budding yeast or pseudohyphae, and trichomonads
10. Apply a coverslip over the slide with sample collected for whiff test with KOH added. Make sure the KOH has had at least 30-60 seconds to react with the sample before observing
11. Examine the slide at 10× and 40× objective for budding yeast, pseudohyphae and blastospores.

Wet prep is going to be considered positive for bacterial vaginosis if clue cells are present; positive for vaginal candidiasis if budding yeast or pseudohyphae are present; positive for trichomonas if trichomonas parasites are present. (Should the study clinician make a presumptive diagnosis of such infections, these subjects will be withdrawn and referred for standard of care treatment. They may re-enroll and begin study activities 14 days after treatment per Section describing the Prohibited Medications.

Following Instructions Will be Given for Whiff Amine Testing (KOH Test) (Summarized procedural steps for these tests are provided for information only; specimen collection and testing shall be performed according to site laboratory SOPs):
1. Apply a portion of the undiluted vaginal material from swab collected in same manner as vaginal pH swab, or one drop of the saline suspension (see Wet Prep Testing), to the surface of a clean glass slide.
2. Add one drop of 10% potassium hydroxide (KOH) directly to the vaginal specimen
3. Holding the slide gently fan the vapor layer (whiff) above the surface of the slide and assess for the presence of volatile amines which have a fishy odor.

Positive: The presence of a fishy odor following addition of KOH to the vaginal specimen. Negative: The absence of a fishy odor following addition of KOH to the vaginal specimen.

Amsel Criteria:

Amsel criteria corresponding to the diagnosis of BV are listed below and subject must be positive in three of these four areas to be diagnosed with bacterial vaginosis.
1. Vaginal pH>4.5
2. Presence of thin, grayish white vaginal discharge
3. Positive Whiff amine test
4. Positive Wet prep Assessment of Vaginal Irritation (Vaginal Comfort):

Prior to collection of swabs for vaginal pH readings, all subjects will be asked to assess their current level of vaginal comfort. They will be asked to rate this assessment using the following criteria and scale, listed in Table 3.

TABLE 3

Adverse events evaluation scale
Vaginal Comfort

| Assessment Criteria | Rating | | | |
|---|---|---|---|---|
| Vaginal pain | None | Mild | Moderate | Severe |
| Vaginal burning | None | Mild | Moderate | Severe |
| Vaginal Itching | None | Mild | Moderate | Severe |
| Vaginal discharge | None | Mild | Moderate | Severe |

While inpatients on Day 0 until discharge on Day 1, research staff will record vaginal comfort assessments in the source documents; for the self-performed 12 hour vaginal pH test and each day following discharge, subjects will record vaginal comfort assessments in their diary (i.e., the Subject Diary), prior to collecting the swab to perform vaginal pH testing. Subjects who rate any vaginal comfort criteria as "Moderate" or higher will be assessed, (following discharge, subjects are instructed to report this information to the Site PI immediately) and if applicable, examined. All criteria assessed as "Mild" or higher will be recorded as an Adverse Event.

Subject Diary:

Each subject will be provided with a subject diary to track adverse events between study visits. Study Coordinator will explain to each subject the importance of the diary. The instruction on maintaining the diary should include what fields have to be completed and how the subject should record data within it. Study coordinator will review the diary prior to discharge and at the final study visit. The subject will record vaginal pH readings (including date and time), vaginal comfort level, any adverse events, as well as noncompliance to activities or medications noted in the subject exclusion list or concomitant medications list at screening (abstaining from sexual intercourse, douching or any form of vaginal suppository or intravaginal device; any antibiotic, antimycotic, or probiotic compounds, oral or intravaginal, used during course of study). For subjects that have consented to the microbiome collection, they will record placement of the swab and its transport container into the freezer. Any deficiencies and attempts to correct these deficiencies should be noted in progress notes (source documents). Study coordinator must ensure that the diaries are returned at the time designated in the study protocol. If a subject diary is not returned, the site should make several attempts to retrieve it. These attempts should be documented in the subject's source documents. The Subject diary will be reviewed by the research staff prior to each vaginal pH sample collection time point while subjects are in the domiciliary unit, and before start of visit-specific procedures at the Day 7 Final Study visit. The diary will be issued to the subject on Day 0, during training session to perform vaginal pH testing, and will be kept by the subjects through Day 7 (Final Study Visit). Diaries will be re-issued to the subject after making a copy for subjects' study record. All returned diaries will become part of the subjects' study record.

The Following Section Describes the Procedures to be Carried Out on Each Visit:

Day 0 (Prior to Admittance to Domiciliary Unit):

Screening Enrollment and admittance to domiciliary unit for dosing (Day 0) may all occur on the same day. Once screened, eligible subjects must be enrolled and admitted to the domiciliary unit for dosing (Day 0) within five (5) days post screening visit. Enrolled subjects who are not admitted within 48 hours of Screening will have some tests/procedures repeated upon admission. It is anticipated that about three subjects will be screened for every two enrolled. Subjects who wish to participate in the trial will be asked to sign and date the Informed Consent and HIPAA Forms prior to any trial specific procedures. All subjects will be provided with a copy of their own signed and dated Informed Consent Form. The principal investigator at the clinical trial site must keep a subject screening log, subject enrollment log and subject identification log for identifying all subjects having signed Informed Consent and HIPAA Forms.

The following will be performed by research staff and/or recorded in the source documents and case report form (CRF):
1. Informed consent and HIPAA completed
2. Additional consent required for participating in the Microbiome collection
3. Evaluation of inclusion and exclusion criteria
4. Evaluate eligibility criteria
5. Demographic data
6. Medical/surgical/gynecologic history
7. Concomitant medication: All medications taken will be recorded in standard data collection forms with attention to drug route, daily dose, duration, start date, stop date and indications.
8. Body height and weight
9. Vital signs measurement (BP, HR, temperature)
10. Pregnancy test (UHCG)
11. Laboratory Testing (Vaginal pH, Microbiome collection, Wet Mount Smear, Whiff test, all performed from vaginal swab—Amsel criteria evaluation from results of these three tests)
12. Gynecologic examination (speculum, performed by clinician)
13. HIV serology (blood draw). If subject has a laboratory result of HIV positive result, this blood draw does not need to be done Day 0 (at the Clinical Trial Site Domiciliary Unit):

Screening, Enrollment and admittance to domiciliary unit for dosing (Day 0) may all occur on the same day. These procedures reflect a cross over from what is completed for screening. The following will be performed and/or recorded in the source documents and CRF:
1. Record any changes in the following since screening visit:
   a. medical/surgical/gynecologic history
   b. adverse events
   c. concomitant medications
2. Vaginal comfort assessment (baseline)
3. Pregnancy test (urine)
4. Vaginal pH (performed by research staff)
5. Vaginal microbiome collection for subjects who consented
6. Gynecologic examination (speculum, performed by clinician)

If the subject withdraws or is terminated (for not meeting all the inclusion/exclusion criteria outlined above) from the study prior to administration of the study product, the procedure described in Alternate Subject Enrollment to Account for Lost to Follow-ups and Withdrawals is followed.

Administration of IP or no treatment based on Group assignment.
1. GROUP A subjects: the exemplary gel formulation (e.g., Acidform or Amphora® Gel) at 5 g dose instilled IVAG
2. GROUP B subjects: the exemplary gel formulation (e.g., Acidform or Amphora® Gel) at 4 g dose instilled IVAG
3. GROUP C subjects: the exemplary gel formulation (e.g., Acidform or Amphora® Gel) at 3 g dose instilled IVAG
4. GROUP D subjects: UPG, 4 g dose instilled IVAG
5. GROUP E subjects: No treatment (For GROUP E (control), treatment is defined as no gel instillation. Time points for subsequent procedures from Day 0 through Day 7 noted as "X hours post-treatment" for this group are defined as number of hours post Day 0 speculum exam.)

One hour post treatment:
1. Vaginal pH (performed by research staff—two samples, two readings)
2. Vaginal comfort assessment (subjects queried)
3. Adverse event reporting; targeted physical exam, if needed, based on symptoms Six hours post treatment:
1. Vaginal pH (performed by research staff—two samples, two readings)
2. Vaginal comfort assessment (subjects queried)
3. Adverse event reporting; targeted physical exam, if needed, based on symptoms
4. Subject training to collect self-obtained vaginal swabs and perform vaginal pH readings on Day 2 through Day 6. (Verification of subject understanding and competency to complete vaginal pH testing documented in source documents prior to discharge of subject)

Twelve (+/−2) hours post treatment:
1. Provide subject with diary to record vaginal pH readings, vaginal comfort levels, and adverse events between visits
2. Vaginal pH (performed by subject, one sample, one reading)
3. Vaginal comfort assessment (subjects queried)
4. Adverse event reporting; targeted physical exam, if needed, based on symptoms Subjects who are not admitted on the same day as Screening, but within 48 hours of Screening, have a urine pregnancy (UHCG) and vaginal pH test, medical/surgical history, concomitant medications, AE assessment and vital signs repeated upon admission administration of IP. If subject has consented to microbiome collection, the swab will again be collected.

Subjects admitted more than 48 hours but up to 5 days post Screening have a urine pregnancy (UHCG), vaginal pH test, speculum exam, vaginal smear for Amsel criteria, medical/surgical history, concomitant medications, AE assessment and vital signs repeated upon admittance prior to administration of IP. If subject has consented to microbiome collection, the swab will again be collected.

Day 1 (at the Domiciliary Unit):
All subjects will remain in the domiciliary unit for assessment of vaginal pH, vaginal comfort, and adverse reactions for a period of 24 (+/−2) hours, or longer as determined by the clinical trial site principal investigator. The following will be performed by the research staff and/or recorded in the source documents and CRF:
1. Vaginal pH and microbiome collection (performed by research staff) at 24 (+/−2) hours post-treatment
2. Demonstrate to subjects who have consented to microbiome collection, the procedure of placing swab in transport container, snapping off of the swab stick, closing lid securely. Instruct subjects to place upright in their −20 freezer for storage
3. Vaginal comfort assessment at 24 (+/−2) hours post-treatment
4. Review subject diary card at 24 (+/−2) hours post-treatment
5. Adverse event reporting at 24 (+/−2) hours post-treatment
6. Review concomitant medications at 24 (+/−2) hours post-treatment
7. Vital signs measurement (BP, HR, temperature) at 24 (+/−2) hours post-treatment
8. Laboratory Testing, performed by research staff at 24 (+/−2) hours post-treatment (Vaginal pH, Wet Mount Smear, Whiff test, all performed from vaginal swab—Amsel criteria evaluation from results of these three tests) (Swab for vaginal pH reading is collected prior to introduction of speculum for gynecologic exam)
9. Gynecologic examination (speculum, performed by clinician) at 24 (+/−2) hours post-treatment
10. Targeted physical examination, if needed based on symptoms
11. Provide supplies to subject for self-obtained vaginal swabs and vaginal pH readings for Days 2 through Day 6
12. Schedule Day 7 Final Study Visit
13. Subject released from domiciliary unit Day 2 (Subject at Home):
The following will be performed and/or recorded in the source documents and CRF:
1. Adverse event reporting (subject records on diary card)
2. Vaginal comfort assessment (subject records on diary card)
3. Vaginal pH (performed by subject) at 48 (+/−4) hours post-treatment (subject records on diary card).
4. In consented subjects, microbiome collection with storage of swab in freezer Day 3 (Subject at Home):
The following will be performed and/or recorded in the source documents and CRF:
1. Adverse event reporting (subject records on diary card)
2. Vaginal comfort assessment (subject records on diary card)
3. Vaginal pH (performed by subject) at 72 (+/−4) hours post-treatment (subject records on diary card).
4. In consented subjects, microbiome collection with storage of swab in freezer Day 4 (Subject at Home):
The following will be performed and/or recorded in the source documents and CRF:
1. Adverse event reporting (subject records on diary card)
2. Vaginal comfort assessment (subject records on diary card)
3. Vaginal pH (performed by subject) at 96 (+/−4) hours post-treatment (subject records on diary card).
4. In consented subjects, microbiome collection with storage of swab in freezer Day 5 (Subject at Home):
The following will be performed and/or recorded in the source documents and CRF:
1. Adverse event reporting (subject records on diary card)
2. Vaginal comfort assessment (subject records on diary card)
3. Vaginal pH (performed by subject) at 120 (+/−4) hours post-treatment (subject records on diary card).
4. In consented subjects, microbiome collection with storage of swab in freezer Day 6 (Subject at Home):
The following will be performed and/or recorded in the source documents and CRF:
1. Adverse event reporting (subject records on diary card)
2. Vaginal comfort assessment (subject records on diary card)
3. Vaginal pH (performed by subject) at 144 (+/−4) hours post-treatment (subject records on diary card)
4. In consented subjects, microbiome collection with storage of swab in freezer Day 7 (+/−24 Hours Post Treatment)
[final study visit at the outpatient center of clinical trial site]: The following will be performed by the research staff and recorded in the source documents and CRF:
1. Review subject diary card
2. Adverse event reporting
3. Review concomitant medications
4. Query subject on current vaginal comfort
5. Laboratory Testing (Vaginal pH, Microbiome collection (in consented subjects), Wet Mount Smear, Whiff test, all performed from clinician obtained vaginal swab—Amsel criteria evaluation from results of these three tests) (Swab for vaginal pH reading is collected prior to introduction of speculum for gynecologic exam)

6. Gynecologic exam (speculum, performed by clinician)
7. Targeted physical examination, if needed based on symptoms In order to allow flexibility to subjects unable to attend the final study visit on Day 7, a grace period of +/−24 hours is allowed for this visit when necessary (168+/−24 hours post treatment).

Unscheduled Visit(s): The subject will be asked to return to the clinical research site for evaluation if she develops symptoms or signs of illness and needs to be evaluated between scheduled visits. A medical history will be taken and a targeted physical examination as dictated by the symptoms. Safety lab or other lab tests will be obtained as deemed necessary by the Site PI. Findings will be documented in the source documents and on an eCRF for unscheduled visits. Adverse event assessment (including SAEs) will be recorded in the source documents and on the eCRF.

Early Termination:

For any subject who has received any amount of the study product and then withdraws or is withdrawn, an early termination visit will be conducted if the subject is willing. All activities listed for Day 7 will be carried out unless medically contraindicated.

Clinical Laboratory Specimen Preparation, Handling and Storage:

All laboratory specimens collected at JHU or MHMC during study visits will be collected and processed by a trained study research team member, following site SOPs and all applicable site and local safety committee safety guidelines. All samples collected on-site will be tested in the research unit; blood for HIV testing will be sent directly to the site laboratory for testing.

Safety Reporting and Safety Monitoring

Regulatory requirements including the FDA regulations, ICH Guidelines for Good Clinical Practice, and EU Clinical Trials Directive set forth safety monitoring and reporting responsibilities of sponsors and Investigators to ensure the safety and protection of human subjects participating in clinical trials.

Responsibilities:

The Site PIs participating in this clinical trial are responsible for and will:

Evaluate subject safety including assessment of adverse events (AEs) for seriousness, severity, and causality,
Notify ClinicalRM and the Sponsor, Evofem, Inc., of SAEs within 24 hours of awareness of event,
Provide detailed written reports, including necessary documentation requested by the Sponsor or IRB/IEC, promptly following immediate initial reports, and
Inform the IRB/IEC of AEs as required by applicable regulatory requirements Adverse Event (AE): Any untoward medical occurrence in a clinical investigation subject who has received a study product intervention and that does not necessarily have to have a causal relationship with the study product. An AE can, therefore, be any unfavorable and unintended sign (including an abnormal laboratory finding, for example), symptom, or disease temporally associated with the use of a study medicinal product, whether or not considered related to the study medicinal product.

Serious Adverse Event (SAE):

An SAE is any adverse event that results in any of the following outcomes:

Death;
Life-threatening (immediate risk of death);
In-patient hospitalization or prolongation of existing hospitalization;
Persistent or significant disability or incapacity;
Congenital anomaly/birth defect;
Important medical events that may not result in death, be life threatening, or require hospitalization may be considered a serious adverse event when, based upon appropriate medical judgment, they may jeopardize the subject and may require medical or surgical intervention to prevent one of the outcomes listed in this definition. Examples of such medical events include allergic bronchospasm requiring intensive treatment in an emergency room or at home, blood dyscrasias or convulsions that do not result in in-patient hospitalization, or the development of drug dependency or drug abuse.

The term "life-threatening" in the definition of SAE refers to an event in which the subject was at risk of death at the time of the event. It does not refer to an event which hypothetically might have caused death if it were more severe.

The term "hospitalization" describes a period of at least 24 hours. Overnight stay for observation, treatment at an emergency room or treatment on an out-patient-basis does not constitute a hospitalization. However, medical judgment must always be exercised and when in doubt, the case should be considered serious.

Non-serious Adverse Event:

A non-serious AE is any AE which does not fulfill the definition of an SAE.

Pre-treatment Adverse Event:

A pre-treatment AE is any untoward medical occurrence arising or observed between informed consent and the initiation of the study product.

Treatment Emergent Adverse Event (TEAE):

A TEAE is any adverse event occurring after the application of the study product and within the time of residual product effect, or a pre-treatment event or pre-existing medical condition that worsens in intensity after the application of study product and within the time of residual product effect. The time of residual product effect is the estimated period of time after the dose of the study product, where the effect of the product is still considered to be present based on change of vaginal pH from baseline.

Unexpected Adverse Reaction:

An adverse reaction, the nature or severity of which is not consistent with the applicable product information (e.g., IND Safety Data).

Safety Reporting Requirements

Reporting Interval:

All AEs and SAEs will be collected and recorded following enrollment. The clinical trial site principal investigator will follow all AEs and SAEs until resolution (return to pretreatment status or stabilization of conditions deemed as chronic) even if this extends beyond the study-reporting period. At any time after the completion of the study, if a clinical trial site principal investigator becomes aware of a serious adverse event that is suspected to be related to the study product, the event will be reported to ClinicalRM, within 24 hours of awareness. ClinicalRM will report the event immediately to the Sponsor. The principal investigator will further ensure that the appropriate IRB has been notified of the reported SAE in a timely manner per internal IRB reporting requirements.

Notification of the Sponsor of Serious Adverse Events:

Any AE that meets a protocol-defined serious criterion, must be submitted by sites within 24 hours of site awareness on an SAE form to ClinicalRM, at the following fax number and uploaded to the ClinicalRM Sponsor SharePoint Site: Other supporting documentation of the event may be requested by the Sponsor, Evofem, Inc. or ClinicalRM and should be provided as soon as possible. The medical monitor and clinical project manager will be notified of the SAE. The medical monitor will review and assess the SAE for regulatory reporting and potential impact on study subject safety and protocol conduct and inform the study Sponsor, Evofem, Inc., according to the specified times for reporting AEs. Evofem, Inc. will inform the regulatory authorities and independent ethics committees (IECs/institutional review boards (IRBs)) in accordance with the local requirements in force and International Conference on Harmonization (ICH) Good Clinical Practice (GCP) [ICH, GCP 2012]. ClinicalRM will notify the Sponsor of any unexpected SAE with suspicion of being related to study drug in accordance with the local requirements. In addition, the Sponsor will be informed of any study related procedure SAE which may warrant a change of any study procedure or halting of the study.

Regulatory Reporting for Studies Conducted Under IND:

Following notification from the Site PI, the Sponsor will report events that are both serious and unexpected and that are associated with study product(s) to the Food and Drug Administration (FDA) within the required timelines as specified in 21 CFR 312.32: fatal and life-threatening events within 7 calendar days (by phone or fax) and all other SAEs in writing within 15 calendar days. All serious events designated as "not associated" to study product(s) will be reported to the FDA at least annually in a summary format.

Investigator's Assessment of Adverse Events:

The determination of seriousness, severity, and causality will be made by the Site PI who is qualified (licensed) to diagnose adverse event information, provide a medical evaluation of adverse events, and classify adverse events based upon medical judgment. This includes but is not limited to physicians, physician assistants, and nurse practitioners.

Assessment of Seriousness:

Event seriousness will be determined according to the protocol definition of an SAE.

Assessment of Severity:

Event severity will be assigned according to the Table of Clinical Events (AEs) for this study. The event may change in severity before resolving. Highest severity per 24 hour block of time and relevant changes in severity will be recorded.

Assessment of Adverse Event Causality:

All AEs will be assessed by the Site PI for relationship to the trial product, independent of whether the adverse event is serious or non-serious AEs, and independent of its severity, using the following directions:

Definite: Good reasons and sufficient documentation to assume direct involvement of the study drug in a causal relationship.

Probable: Good reasons and sufficient documentation to assume a causal relationship.

Possible: A causal relationship is conceivable and cannot be dismissed.

Unlikely: The event is most likely related to an etiology other than the study product Unrelated: The event is related to an etiology other than the study product.

Adverse Events of Interest: In a double blinded, Phase 1 clinical safety trial six subjects who were treated with the exemplary gel formulation (e.g., Acidform or Amphora® Gel)1 reported no complaints and no vulvovaginal or cervical irritation. No evidence of such inflammation was observed by clinicians on visual or colposcopic inspection after six daily applications of IVAG the exemplary gel formulation (e.g., Acidform or Amphora® Gel) in a previous study. In a Phase I, placebo-controlled, randomized, closed-label study involving 14 days of twice-daily product exposure to the exemplary gel formulation (e.g., Acidform or Amphora® Gel) or KY® Jelly intravaginally twice-daily for 14 consecutive days between menses. About two thirds of the exemplary gel formulation (e.g., Acidform or Amphora® Gel) group compared to about one-third of the KY® Jelly group reported at least one symptom of genital irritation. These symptoms, in general, were mild and included genital pain (burning, irritation, etc.), pruritus, pelvic cramping, vaginal candidiasis, and spotting. The three latter symptoms occurred later in the study (after multiple twice daily dosing). Safety data from a much larger Phase III study showed similar minor adverse events when the exemplary gel formulation (e.g., Acidform or Amphora® Gel) gel was applied regularly Adverse Event's Outcome Measures:

The outcome of all AEs will be reported based on the following definitions, independent of whether they are serious or non-serious AEs, their severity, or their relationship to the trial product:

Recovered: Fully recovered, or by medical or surgical treatment the condition has returned to the level observed at the first study related activity after the subject signed the informed consent.

Recovering: The condition is improving and the subject is expected to recover from the event. This term should only be used when the subject has completed the study.

Recovered with sequelae: As a result of the AE, the subject suffered persistent and significant disability/incapacity (e.g. became blind, deaf, paralyzed). Any AE recovered with sequelae should be rated as an SAE.

Not recovered

Fatal

Unknown: This term should only be used in cases where the subject is lost to follow-up.

Process for Documentation of Events of Interest:

Based on the safety profile of the exemplary gel formulation (e.g., Acidform or Amphora® Gel) observed in previous Phase I, Phase II, and Phase III studies, an assessment plan for anticipated adverse events will be implemented. All AEs will be documented on the standard adverse event forms. Adverse events forms for cutaneous AE grade 3 or higher will be emailed to the Sponsor's representative, ClinicalRM, within 24 hours (non-serious or serious). The reporting of an AE grade 3 or higher will prompt follow-up diagnostic work-up (e.g., physical examinations, vital signs, descriptive assessment, subject diary and clinical laboratory work). If the cutaneous AE is grade 3, subjects will be seen twice weekly until the severity is reduced to grade 2 or less at two consecutive visits and not getting worse.

Other Safety Considerations:

Any significant worsening or new findings noted during the final gynecological examination or any other potential safety assessments performed during the course of the study, whether or not they are required by the protocol, should be recorded on the appropriate AE form.

Pregnancy:

Woman of childbearing potential can be enrolled. However, women must agree to abstain from sexual intercourse over the duration of the study period. If there is any question that a subject will not be reliable in the adherence to this requirement, she should not be entered into the study. Study subjects must be instructed to notify the clinical trial site principal investigator immediately if they suspect pregnancy during the course of the study and for a period of four weeks following study discharge. The Site PI must report any pregnancy during the study to ClinicalRM. Study subjects will give consent upon enrollment that the Site PI will report any pregnancy during the study to ClinicalRM and that she will be asked to provide information about her pregnancy, delivery, and the health of her infant until age one month. The Site PI must report information on pregnancy and follow-up within 14 calendar days of obtaining the information using the Pregnancy Form and the Pregnancy Follow-up Form, respectively. Pregnancy complications must be recorded as AEs. If the infant has a congenital anomaly or birth defect, the anomaly or defect must be reported and followed as an SAE.

Safety Oversight Contingency Plan:

Due to the Sponsor's experience with the IP and awareness of SAE probability based on past study data, no Safety Monitoring Committee (SMC) will be established for this study. In the event that SAEs occur at a rate different than anticipated, the study will be halted and a SMC initiated.

Follow-up of Adverse Events:

During and following a subject's participation in a clinical study, the Site PI/institution should ensure that adequate medical care is provided to the subject for any AEs, including clinically significant laboratory values related to the study. The Site PI/institution should inform the subject when medical care is needed for AEs of which the Site PI becomes aware. The post-treatment follow-up period for reporting new adverse events will continue until the last follow-up visit. All non-serious AEs classified as severe or possibly/probably related or definitely related to the study product must be followed until the subject has recovered and all queries have been resolved. However, cases of chronic conditions can be closed with an outcome of "recovering" or "not recovered". If a subject dies from another event, these cases can be closed with an outcome of "not recovered." All other non-serious AEs must be followed until the outcome of the event is "recovering" (for chronic conditions), or until the PI considers the AE to be stable, whichever comes first, and until all queries related to these AEs have been resolved. If a subject dies from another event, these cases can be closed with an outcome of "not recovered." The clinical trial site principal investigator must ensure that the worst case severity and seriousness is kept consistent through the series of AE forms and related AE follow-up form(s). The principal investigator must enter follow-up information about non-serious AE on the AE form within the CRF. Queries or follow-up requests from ClinicalRM should be responded to within 14 calendar days, unless otherwise specified. The Site PI must forward follow-up information on SAEs to ClinicalRM within 5 calendar days of obtaining the request for follow-up information. All SAEs must be followed until the outcome of the event is recovered, recovered with sequelae or fatal and until all queries have been resolved. For cases of chronic conditions and cancer or if the subject dies from another event follow-up until the outcome categories are "recovered", "recovered with sequelae" or "fatal" is not required, as these cases can be closed with an outcome of "recovering" or "not recovered."

Halting Criteria/Rules:

The safety halting criteria rules are:
1. Death of an enrolled subject unless unequivocally not attributable to study drug (e.g., traumatic injury)
2. Occurrence of a life-threatening allergic/hypersensitivity reaction (anaphylaxis) within 48 hours of dosing, requiring hemodynamic support with vasoactive medications or mechanical ventilation the signs/symptoms will include any of the following: bronchospasm, dyspnea, wheezing, stridor, hypoxemia urticaria, angioedema, hives, and facial or oropharyngeal edema
3. An overall pattern of symptomatic or clinical events that the sponsor, site PI or Medical Monitor consider associated with study drug and that may appear minor in terms of individual events, but that may collectively represent a serious potential concern for safety.

If trial is prematurely terminated or suspended, the Sponsor shall inform investigators, regulatory authorities and IRB of the reason for halting.

Example 2: A Randomized, Placebo Controlled Pilot Study to Determine the Effect and Duration of One Exemplary Gel Formulation (e.g., Acidform or Amphora® Gel) on Vaginal pH Protocol of Example 1 was followed, unless otherwise indicated in the present example. The following amendments were made to the protocol of Example 1:

The randomization process was amended from the methodology stated in the protocol of Example 1. The protocol specified that the biostatistician would transfer the randomization listing to a study pharmacist. However, this process was modified to specify that the biostatistician would transfer the randomization listing to a designated unblinded data management administrator prior to the start of the study.

To allow for flexibility to both subjects and domiciliary staff, the following windows were permitted for sample collections at post-treatment time points: 1 hour+30 minutes, 6 hours±30 minutes, 12 hours±2 hours, 24 hours±2 hours.

For sample collections at baseline and post-treatment at 1, 6, 12, and 24 hours, up to 3 swab collections could be taken to allow for measurement of pH using pH papers covering different pH ranges.

Analysis of the data on vaginal microbiome was handled by the microbiome investigator.

One hundred and five volunteer women (at least 20 per treatment group) were treated with either Acidform, 5 g dose (Group A), Acidform, 4 g dose (Group B), Acidform, 3 g dose (Group C), placebo, 4 g (Group D), or no treatment (Group E). For the 3 treatment groups receiving Acidform (at either 3, 4, or 5 g), treatment was defined as speculum examination plus administration of Investigational Product (IP). For the placebo treatment group, treatment was defined as speculum examination plus administration of placebo. For Group E, the control, no treatment, was defined as speculum examination only.

Because vaginal pH values have been shown to vary by ethnicity, the intention was to recruit at least 13 subjects in each group who were of either African American or Hispanic descent. Routine screening tests were performed on admission, and subjects were assessed for asymptomatic BV via vaginal swabs obtained for grading by Amsel criteria.

A direct vaginal pH reading from each subject was obtained by research staff prior to the speculum examination, as well as 1 hour, and 6-hours post-treatment (Day 0). Direct vaginal readings taken at the 1 hour and 6-hours post-treatment time points were taken on specimens collected from 2 different positions in the vagina, to allow for potentially incomplete distribution of the IP or placebo immediately following administration. Both readings were included in the full data analysis sets. At the 6-hour post-treatment time point subjects were trained on self-collecting vaginal swabs and how to perform the vaginal pH test. At 12-hours post-treatment, whilst still in the domiciliary clinic, subjects performed the vaginal pH test themselves using self-obtained swabs, and recorded their results for clinician review.

Clinicians collected adverse event (AE) assessment data while subjects were in the domiciliary unit, at each post-treatment vaginal pH testing time point (1, 6, 12, and 24-hours post-treatment).

Additional vaginal microbiome collection was carried out for all the women who gave consent. The same swab for vaginal pH at Baseline/Screening, post 24-hour treatment and Days 2 through 7 were used for the microbiome analysis. Research staff obtained the readings from swabs taken at Baseline/Screening (a repeat pH/microbiome swab was taken if screening and admission to the domiciliary unit did not occur on the same day), post 24-hour treatment and Day 7 (Table 4).

Subjects stayed overnight in the domiciliary units, and vaginal pH, microbiome collection (from consented subjects), and Amsel criteria were measured by research staff at 24-hours post-treatment prior to discharge on Day 1. Subjects were discharged with the appropriate pH testing supplies and a diary. All women had to agree to abstain from sexual intercourse, douching, and use of any intravaginally applied products or devices until after their final study visit on Day 7.

Subjects measured their vaginal pH and carried out microbiome collection at 24 (±4) hour intervals for 5 days (Days 2 to 6) as outpatients and recorded the pH test results, any change in vaginal comfort, and confirmation of having taken the microbiome swab in the diary provided. Subjects also recorded any activities engaged in, along with the day this occurred, that were listed in the study exclusion criteria.

On Day 7 (±24 hours), subjects returned to the clinic with their diary and swab transport containers. Clinic staff measured subjects' vaginal pH and Amsel criteria, and questioned them about any vaginal comfort (vaginal comfort assessment) over the course of the study (as per the self-recording in their diaries).

Figure 2:
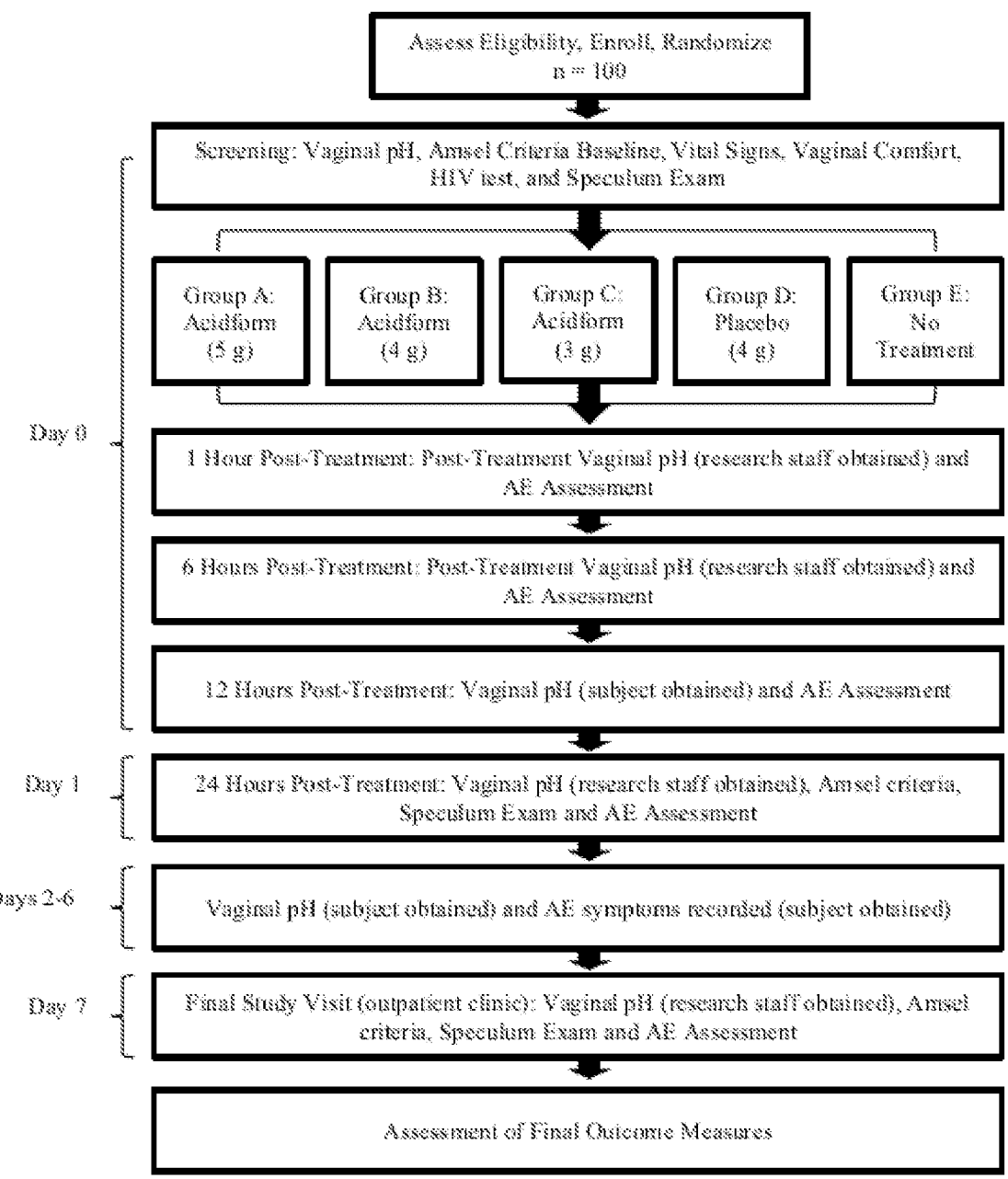
FIG. 2 illustrates an exemplary study design for a phase 1 randomized placebo controlled pilot study to determine the effect and duration of an intravaginal composition, as described in the present disclosure, on vaginal pH.

The Intervention and Follow-Up Period was defined as Day 0 to Day 7 in the Schedule of Events (Table 4). The protocol-defined period of observation was 8 days (FIG. 2).

TABLE 4

Study Schedule

| Study Day | Study Event |
|---|---|
| −5 to 0 | Screening visit |
| 0 | Enrollment and admittance to domiciliary unit Administration of study treatment |
| 1 | Inpatient follow-up and discharge |
| 2-6 | Subject self-assessments at home |
| 7 ± 1 | Outpatient follow-up visit |

TABLE 5

Study Protocol Chart

| Procedure Visit type | Screening/ Enrollment[1] Screening (clinic) | Upon admit | Day 01 1 hr post- admin Hospital admit | 6 hr post- admin | 12 hr post- admin | Day 1 Hosp admit | Day 2 N/A home | Day 3 N/A home | Day 4 N/A home | Day 5 N/A home | Day 6 N/A home | Day 7[3] Outpatient clinic |
|---|---|---|---|---|---|---|---|---|---|---|---|---|
| Written informed consent/HIPAA | X | | | | | | | | | | | |
| Evaluation inclusion/ exclusion criteria | X | | | | | | | | | | | |
| Demographic data | X | | | | | | | | | | | |
| Medical/surgical history[1] | X | X[1] | | | | | | | | | | |
| Body height and weight | X | | | | | | | | | | | |
| Concomitant medication | X | X[1] | | | | | | | | | | X |
| Vital signs (BP, HR, temperature)[1] | X | X[1] | | | | X | | | | | | |
| Gynecologic exam[1] (speculum) | X | X[1] | | | | X | | | | | | X |
| Vaginal comfort assessment (subject recorded) | | X | X | X | X | X | X | X | X | X | X | X |
| Vaginal pH[1] (research staff obtained) | X | X | X[2,6] | X[2,6] | X[2,6] | | | | | | | X |
| Vaginal microbiome (research staff obtained) | X | X | | | | X | | | | | | X |
| Vaginal pH (self- obtained) | | | | | X[6] | | X[4] | X[4] | X[4] | X[4] | X[4] | |
| Vaginal microbiome (subject obtained swab) | | | | | | | X | X | X | X | X | |
| Amsel criteria[1] (research staff obtained swab) | X | X[1] | | | | X | | | | | | X |

TABLE 5-continued

Study Protocol Chart

| | | Day 01 | | | | | | | | | |
|---|---|---|---|---|---|---|---|---|---|---|---|
| Procedure Visit type | Screening/ Enrollment[1] Screening (clinic) | Upon admit Hospital admit | 1 hr post-admin | 6 hr post-admin | 12 hr post-admin | Day 1 Hosp admit | Day 2 N/A home | Day 3 N/A home | Day 4 N/A home | Day 5 N/A home | Day 6 N/A home | Day 7[3] Outpatient clinic |
| Urine pregnancy test[1] | X[1] | X[1] | | | | | | | | | | |
| HIV serology | X | | | | | | | | | | | |
| Treatment (Groups A, B, C, D and E)[3] | | X | | | | | | | | | | |
| Adverse event reporting (if applicable) | | X | X | X | X | X | X | X | X | X | X | X |
| Subject diary review | | | | | | X | | | | | | X |
| Targeted physical exam (if needed based on symptoms) | X | | | | | X | | | | | | X |

[1]Screening, Enrollment and admittance to domiciliary unit for dosing (Day 0) could all occur on the same day. Alternatively, once screened, subjects could be enrolled and admitted for dosing (Day 0) up to 5 days post screening Visit:
Subjects who were not admitted on the same day as Screening, but within 48 hours of Screening, had a urine pregnancy (UHCG) and vaginal pH test, medical/surgical history, concomitant medications, and vital signs repeated upon admission. If the subject consented to Microbiome collection, the swab was again collected.
Subjects admitted more than 48 hours up to 5 days post Screening had a UHCG, vaginal pH test, speculum exam, vaginal smear for Amsel criteria, medical/surgical history, concomitant medication, and vital signs repeated upon admittance. If the subject consented to Microbiome collection, the swab was again collected.
[2]For sample collections at baseline and post-treatment at 1, 6, 12, and 24 hours, up to 3 swab collections may be taken to allow for measurement of pH using pH papers covering different pH ranges.
[3]Groups A, B and C - IP (Acidform) administered following all screening tests and baseline vaginal pH test; Group D - Placebo administered following all screening tests and baseline vaginal pH test; Group E - no treatment following all screening tests and vaginal pH test.
[4]In order to allow flexibility to subjects in their daily schedules, pH readings at X-hours post treatment ± 4 hours is allowed.
[5]In order to allow flexibility to subjects unable to attend the final study visit on Day 7, a grace period of ± 24 hours was allowed for when this visit was necessary.
[6]In order to allow flexibility for both subjects and domiciliary staff, the following windows were permitted for sample collection at post treatment: 1 hour + 30 minutes, 6 hours ± 30 minutes, 12 hours ± 2 hours, 24 hours ± 2 hours.
BP = blood Pressure,
HIPAA = Health Insurance Portability and Accountability Act,
HIV = human immunodeficiency virus,
Hosp = Hospital,
HR = heart rate,
N/A = not applicable.

[1]Screening, Enrollment and admittance to domiciliary unit for dosing (Day 0) could occur on the same day. Alternatively, once screen, subjects could be enrolled and admitted for dosing (Day 0) up to post screening Visit:

Subjects who were not admitted on the same day as Screening but within 48 hours of Screening, had a urine pregnancy (UHCG) and vaginal pH test, medical/surgical history, concomitant medication, and vital signs repeated upon admission. If the subject consented to Microbiome collection, the swab was again collected.

Subjects admitted more than 48 hours up to 5 days post Screening had a UHCG, vaginal pH test, speculum exam, vaginal smear for Amsel criteria, medical surgical history, concomitant medication, and vital signs upon admittance. If the subject consented to Microbiome collection, the swab was again collected.

[2]For sample collectiosn at baseline and post-treatment at 1, 6, 12, and 24 hours, up to 3 swab collections may be taken to allow for measurement of pH using pH papers covering different pH ranges. [3]Groups A, B and C—IP (Acidform) administered following all screening tests and baseline vaginal pH test; Group—Placebo administered following all screening tests and baseline vaginal pH test; Group E—no treatment following all screening tests and vaginal pH test.
[4]In order to allow flexibility to subjects in their daily schedules, pH readings at X-hours post treatment ± 4 hours is allowed.
[5]In order to allow flexibility to subjects unable to attend the final study visit on Day 7, a grace period of ±24 was allowed for when this visit was necessary.
[6]In order to allow flexibility for both subjects and domiciliary staff, the following windows were permitted for sample collection at post treatment: 1 hour ± 30 minutes, 6 hours ± 30 minutes, 12 hours ± 2 hours, 24 hours ± 2 hours.
BP = blood Pressure, HIPAA = Health Insurance Portability and Accountability Act, HIV = human immunodeficiency virus, Hosp = Hospital, HR = heart rate, N/A = not applicable.

Study Design, Including the Choice of Control Groups

This was a Phase 1, randomized, placebo-controlled, double-blind, multi-center study.

Subjects were randomized in a 1:1:1:1:1 fashion across the 5 treatment groups. Simple randomization was performed using SAS®, and all documentation of this procedure and output was saved with the study biostatistician's files until the end of the study. Prior to the start of the study, the randomization list was generated by the study biostatistician and transferred to a
designated unblinded data management administrator. There was planned randomization for 15 alternates, if required.

This study had 5 treatment groups: Acidform 5 g, Acidform 4 g, Acidform 3 g, placebo 4 g, and no treatment. Study subjects in Groups A, B, C, and D (Acidform 5 g, 4 g, 3 g, and placebo, respectively) remained blinded to their treatment assignment throughout the entire duration of the study. The Sponsor, Evofem, Inc., prepared IP as well as placebo, and supplied these products in ready to dispense status.

Three doses of Acidform (3 g, 4 g, and 5 g) were chosen, based on previous studies, to assess if there was any difference in the effect each of them had on vaginal pH and the duration of this effect. Universal placebo gel (UPG) was chosen as a comparator. In addition, a no-treatment group was included, not only to differentiate between the effect the 3 doses of Acidform, placebo and no treatment had on vaginal pH, but also to monitor any natural changes in vaginal pH and microbiome over a 7-day period (the duration of the study).

Study was double-blinded to remove any potential bias in the results.

This study was conducted at 2 sites across the United States (US) and results were compiled separately for each center and combined for overall results.

Selection of Study Population

Inclusion Criteria

To be considered eligible, all the following criteria must have been met at baseline:
1. Female subjects between 18 and 45 years, inclusive;
2. Ability to understand the consent process and procedures;
3. Agree to be available for all study visits;
4. Written informed consent in accordance with institutional guidelines;
5. Negative pregnancy test;
6. Able and willing to comply with all study procedures;
7. Have not engaged in sexual intercourse, douching, or used any form of vaginal suppository or intravaginal device for 24 hours prior to enrollment;
8. Agree to abstain from sexual intercourse, douching, or any form of vaginal suppository or intravaginal device use during the course of the study;
9. Report menstrual cycle regularity (25-day to 35-day menstrual cycles);
10. Test negative for BV or are positive but asymptomatic. (BV positive subjects will be referred for treatment at or following the Day 7 follow-up visit).

Exclusion Criteria

Subjects who met any of the following criteria at baseline were ineligible for participation in the study:
1. Participation in any study with an investigational compound or device within 30 days prior to signing informed consent form;
2. Active drug or alcohol use or dependence that, in the opinion of the investigator, would interfere with adherence to study protocol;
3. Any other medical condition(s) that, in the judgment of the investigator, might interfere with the study or require treatment that might interfere with the study;
4. Family member of the investigation study staff;
5. Pregnant or breastfeeding;
6. Inability to provide informed consent;
7. A subject with a history or expectation of noncompliance with medications or treatment protocol;
8. Women with symptoms of urinary tract infection (UTI), symptomatic BV, yeast infection or STI reported or observed during examination or based on laboratory testing performed;*

*Should the study clinician make a presumptive diagnosis of such infections, these subjects will be withdrawn, referred for standard of care treatment, but will not be followed as part of this study. They may be re-screened for potential enrollment 14 days after treatment per protocol, Prohibited Medications, if all other screening criteria are met.

9. Women who regularly use douches, vaginal medications or suppositories, feminine sprays, genital wipes or contraceptive spermicides, or report abnormal vaginal discharge in the 48 hours prior to screening;
10. Women who are menstruating or who would expect to menstruate during the study;
11. Women who are currently using contraceptives that are directly delivered to the vaginal mucosa, such as NuvaRing;
12. Any specific condition that, in the judgment of the investigator, precludes participation because it could affect subject safety.

Removal of Subjects from Therapy or Assessment

All subjects had the right to withdraw formal consent without prejudice at any time during the study. If a subject withdrew formal consent, the investigator was to make a reasonable effort to determine the cause for withdrawal of consent. For these subjects, as well as all other subjects who required permanent discontinuation of study drug, the investigator was to make a reasonable effort to complete all required study procedures.

The subject's participation in this clinical study may have been prematurely discontinued as a result of:
Development of any Exclusion Criteria;
Pregnancy or breastfeeding;
Request by subject to terminate participation;
Requirement for prohibited treatment (see Exclusion Criteria) before Day 7;
Treatment-related toxicity;
Failure to adhere to requirements of the protocol including treatment and safety monitoring;
Lost to follow-up;
Request of primary care provider;
At the request of the IRB/Ethics commit, FDA, or the Sponsor;
Incarceration;
The subject's well-being, based on the opinion of the Site PI.

If a subject discontinued study participation prematurely, the following procedures were to be completed:
Reason for discontinuation must be documented in the source documents and eCRFs;
Subject to be contacted and encouraged to return for a follow-up visit (with subject's consent) for safety;
Subject asked to complete an end-of-study evaluation (all procedures from Final Study Visit, Day 7).

If an AE or SAE occurred, protocol-specified safety follow-up procedures should be undertaken, and the subject encouraged to receive appropriate care under medical supervision until the symptoms of any AE resolve or the subject's condition becomes stable.

Treatments

Treatments Administered

Study treatments were provided in pre-filled, single use applicators, sealed in a foil overwrap. The research study kit contained a group of overwrapped applicators placed into a standard white cardboard box along with instruction for use.

This was a single dose study, with study drug administered by the study clinician on Day 0. Subjects were double-blinded to receive either Acidform 5 g, 4 g, or 3 g, or placebo 4 g. Subjects in the no-treatment group received no treatment and were aware that they were not receiving IP.

Identity of Investigational Product(s)

The following products were used in this study and provided blinded by the Sponsor:

Acidform; active ingredients: L-lactic acid, USP; citric acid, USP; and potassium bitartrate, USP. All 3 active ingredients are designated Generally Regarded As Safe (GRAS) (21 CFR Part 184) and found in many FDA-approved vaginally applied products in percentages similar to or less than those utilized in Acidform.

Acidform, 3 g, Lot number #00138, manufactured by Swiss American Products, Carollton, Tex.

Acidform, 4 g, Lot number #00139, manufactured by Swiss American Products, Carollton, Tex.

Acidform, 5 g, Lot number #00140, manufactured by Swiss American Products, Carollton, Tex.

Placebo; ingredients: Hydroxyethylcellulose (Natrasol 250 HX Pharm), sodium chloride, sodium hydroxide, sorbic acid and purified water adjusted to pH 4.5; Lot number #KAC-C, manufactured by DPT Laboratories, San Antonio, Tex.

Method of Assigning Patients to Treatment Groups

The randomization was performed using SAS®, and all documentation of this procedure and output was saved with the study biostatistician's files until the end of the study.

The randomization list was generated by the study biostatistician and transferred to a designated unblinded data management administrator prior to the start of the study.

A total of 105 subjects were randomized in a 1:1:1:1:1 fashion across the 5 study groups. Up to 15 alternates were available to replace study subjects that dropped out.

Selection of Doses in the Study

The IP, Acidform, has been studied as an intravaginally administered contraceptive gel in the 5 g pre-filled applicator presentation (Study of the Contraceptive Efficacy and Safety of Amphora® Gel Compared to Conceptrol Vaginal Gel, Phase III, ClinicalTrials.gov ID #NCT01306331, completion date June 2014).

Three single doses of Acidform were chosen for this study, 5 g, 4 g, and 3 g. This study assessed the effect of a single dose of Acidform on vaginal pH over 7 days. Several dose finding studies involving Acidform have already been conducted for contraception.

A 4 g dose of standard placebo gel used in clinical trials was chosen for use in this study as an inert comparator. It is an isotonic non-buffering gel, pH adjusted to 4.5. In clinical trials, this placebo has been shown to be safe and acceptable when used up to twice daily for 14 days.

Inclusion of a no-treatment group allowed for direct comparisons to see if Acidform at any of the 3 doses (3 g, 4 g, or 5 g) had an effect on vaginal pH. In addition, comparison between any of the doses of Acidform with no treatment enabled PIs to observe any potential effect of Acidform on the prevention of BV in subjects without BV or who were asymptomatic.

Selection and Timing of Dose for Each Patient

This was a single dose study. The study product (Acidform, 3 g, 4 g, 5 g, or placebo) was administered intravaginally by the study clinician on Day 0, following subject admission to the domiciliary unit. Gel administration occurred using the pre-filled applicator after the gynecologic examination.

Blinding

Study subjects in Groups A, B, C, and D (Acidform 5 g, 4 g, 3 g, and placebo, respectively) remained blinded to their treatment assignment for the entire duration of the study. The Sponsor, Evofem, Inc., prepared IP as well as placebo, and supplied these products in ready to dispense status.

The process for the preparation of the randomization for the study ensured that the study biostatistician was blinded to study treatment assignments. The study biostatistician remained blinded until after the study database had been finalized and locked, and written instructions were provided for unblinding.

Prior and Concomitant Therapy

Standard medical treatment(s) taken by the subject upon study entry were maintained throughout the study. Concomitant medications were assessed and included and any medication taken during the study, including all over the counter medications, vitamins, and nutritional supplements. Information collected for each concomitant medication included, at a minimum: start date, stop date, or continuing, and indication.

Subjects must not have been currently taking or applying, either oral or intravaginal, or have taken or applied for 14 days prior to screening, any antibiotics, antimycotics, or probiotic compounds.

Treatment Compliance

Since the study drug was administered by the study clinician on Day 0, there was 100% treatment compliance across all groups.

Clinicians collected AE assessment data at each post-treatment vaginal pH testing time point while subjects were in the domiciliary unit (1, 6, 12, and 24-hours post-treatment).

Subjects were discharged on Day 1 with the appropriate pH testing supplies and a diary. On Day 2 through Day 6, inclusive, subjects collected their own vaginal swabs and recorded their vaginal pH, and any AE in the subject diary. On Day 7, subjects returned to the clinic for their Final Study Visit. Compliance was assessed using the diary and collected vaginal swabs.

Efficacy and Safety Variables

Efficacy and Safety Measurements Assessed and Flow Chart

Summaries for the vaginal pH data were provided for each evaluation time point by treatment group and overall, as well as for all active treatment groups combined. These summaries included the changes from baseline.

Comparisons across the treatment groups with respect to change from baseline in vaginal pH were performed using analyses of variance (ANOVA). The incorporation of the baseline vaginal pH score into these analyses was explored. Post-ANOVA pairwise comparisons of each study treatment versus the placebo treatment, and versus no treatment was also assessed.

Graphic displays were compiled to illustrate the mean vaginal pH per treatment group at each assessment time point, and the mean change from baseline in mean vaginal pH per treatment group at each post-baseline assessment time point.

Amsel criteria were assessed as a potential indicator of BV infection. These assessments consisted of YES/NO indications for the presence of each of the following:

Vaginal pH>4.5;
Presence of thin, grayish white vaginal discharge;
Positive wet prep;
Positive whiff amine test.

Based on these individual criteria, a derived overall result (positive/negative) was reported. Categorical summaries for each Amsel criterion, as well as for the overall result, was compiled for each assessment time point by treatment group and overall, as well as for all active treatment groups combined.

Details of the assessments and procedures conducted throughout the study are provided by procedure/assessment type and day, in Table 5.

Appropriateness of Measurements

The efficacy and safety measurements in this example are widely used and generally recognized as reliable, accurate, and relevant.

Primary Efficacy Variable(s)

Primary Efficacy Variables

The primary efficacy endpoint was assessment of change in vaginal pH and the duration of this change from baseline, post-administration of a single dose of Acidform or placebo, or no treatment.

Secondary Efficacy Variables

Secondary efficacy endpoints included the following:

Assessment of the effect of a single dose of Acidform or placebo, or no treatment on asymptomatic BV, based on Amsel criteria.

Assessment of the effect of a single dose of Acidform on the vaginal microbiome.

Data Reporting

Data for this study included reported symptoms (including vaginal comfort levels), AEs, clinical laboratory data, gynecological examination, whiff test, wet prep specimen, and clinician and subject-obtained pH values.

Clinical data was entered directly from the source documents, including the subject diary, to the data management system. CRAs performed source verification and query generation. CRAs worked with the Data Manager and site personnel to freeze data prior to analysis. AEs, medical history, and medications were coded using MedDRA® 17 (or higher) and WHO drug dictionaries.

Study Patients

Disposition of Patients

In total 105 subjects were enrolled in the study and all subjects were randomized 1:1:1:1:1 to one of the 5 treatment groups. All subjects received treatment, either a single dose of IP or placebo, or no treatment on Day 0.

Five subjects discontinued the study, all from Acidform treatment groups: 3 subjects were lost to follow-up and 2 subjects discontinued because menses came on during the study (categorized as "other" in Table 6). No subjects discontinued the study due to an AE or SAE.

TABLE 6

Patient Disposition

| | Acidform (5 g) n = 22 | Acidform (4 g) n = 21 | Acidform (3 g) n = 21 | Placebo (4 g) n = 20 | No-Treatment n = 21 |
|---|---|---|---|---|---|
| Number of subjects | | | | | |
| Total Enrolled | 22 | 21 | 21 | 20 | 21 |
| Total Randomized | 22 | 21 | 21 | 20 | 21 |
| Total Treated | 22 | 21 | 21 | 20 | 21 |
| Included in Safety Population | 22 (100%) | 21 (100%) | 21 (100%) | 20 (100%) | 21 (100%) |
| Completed | 21 (95.5%) | 19 (90.5%) | 19 (90.5%) | 20 (100%) | 21 (100%) |
| Discontinued | 1 (4.5%) | 2 (9.5%) | 2 (9.5%) | 0 | 0 |
| Reasons for Discontinuation | | | | | |
| Adverse Event | 0 | 0 | 0 | 0 | 0 |
| Protocol Violation | 0 | 0 | 0 | 0 | 0 |
| Withdrawal of Consent | 0 | 0 | 0 | 0 | 0 |
| Lost to Follow-Up | 1 (100%) | 2 (100%) | 0 | 0 | 0 |
| Other | 0 | 0 | 2 (100%) | 0 | 0 |

The Safety Population included all subjects who received any amount of study treatment, and all subjects who were randomized to the no-treatment group.
Percentages for primary categories are based on the number of subjects who were enrolled to the indicated treatment group. Percentages for subcategories are based on the number of subjects in the primary category being described. Percentages for reasons for discontinuation are based on the total number of subjects who discontinued among those subjects enrolled in the treatment group being summarized.

Demographic and Other Baseline Characteristics

A summary of demographic and baseline characteristics for the population is presented in Table 7.

TABLE 7

Demographics and Baseline Characteristics for Overall Study Population

| | Acidform (5 g) n = 22 | Acidform (4 g) n = 21 | Acidform (3 g) n = 21 | Placebo (4 g) n = 20 | No-Treatment n = 21 |
|---|---|---|---|---|---|
| Age (years) | | | | | |
| n | 22 | 21 | 21 | 20 | 21 |
| Mean (SD) | 31.62 (7.11) | 28.57 (7.20) | 28.12 (5.40) | 30.42 (6.47) | 30.21 (6.45) |
| Median | 30.30 | 27.10 | 26.40 | 31.20 | 30.00 |
| Min, Max | (20.4, 45.6) | (18.8, 44.5) | (19.0, 38.9) | (19.7, 45.0) | (22.1, 46.0) |
| Gender | | | | | |
| Male | 0 | 0 | 0 | 0 | 0 |
| Female | 22 (100%) | 21 (100%) | 21 (100%) | 20 (100%) | 21 (100%) |
| Race | | | | | |
| White | 10 (45.5%) | 6 (28.6%) | 11 (52.4%) | 11 (55.0%) | 7 (33.3%) |
| Black or African American | 10 (45.5%) | 11 (52.4%) | 8 (38.1%) | 6 (30.0%) | 12 (57.1%) |
| American Indian/Alaskan Native | 0 | 0 | 0 | 0 | 0 |
| Native Hawaiian or Other Pacific Islander | 0 | 0 | 0 | 0 | 0 |

TABLE 7-continued

Demographics and Baseline Characteristics for Overall Study Population

|  | Acidform (5 g) n = 22 | Acidform (4 g) n = 21 | Acidform (3 g) n = 21 | Placebo (4 g) n = 20 | No-Treatment n = 21 |
| --- | --- | --- | --- | --- | --- |
| Asian | 1 (4.5%) | 0 | 1 (4.8%) | 0 | 1 (4.8%) |
| Other | 1 (4.5%) | 4 (19.0%) | 1 (4.8%) | 3 (15.0%) | 1 (4.8%) |
| Ethnicity |  |  |  |  |  |
| Hispanic or Latino | 6 (27.3%) | 6 (28.6%) | 2 (9.5%) | 6 (30.0%) | 3 (14.3%) |
| Not Hispanic or Latino | 16 (72.7%) | 15 (71.4%) | 19 (90.5%) | 14 (70.0%) | 18 (85.7%) |

Percentages are based on the number of subjects in the indicated treatment group.

Efficacy Results and Tabulations of Individual Subject Data

Figure 3:
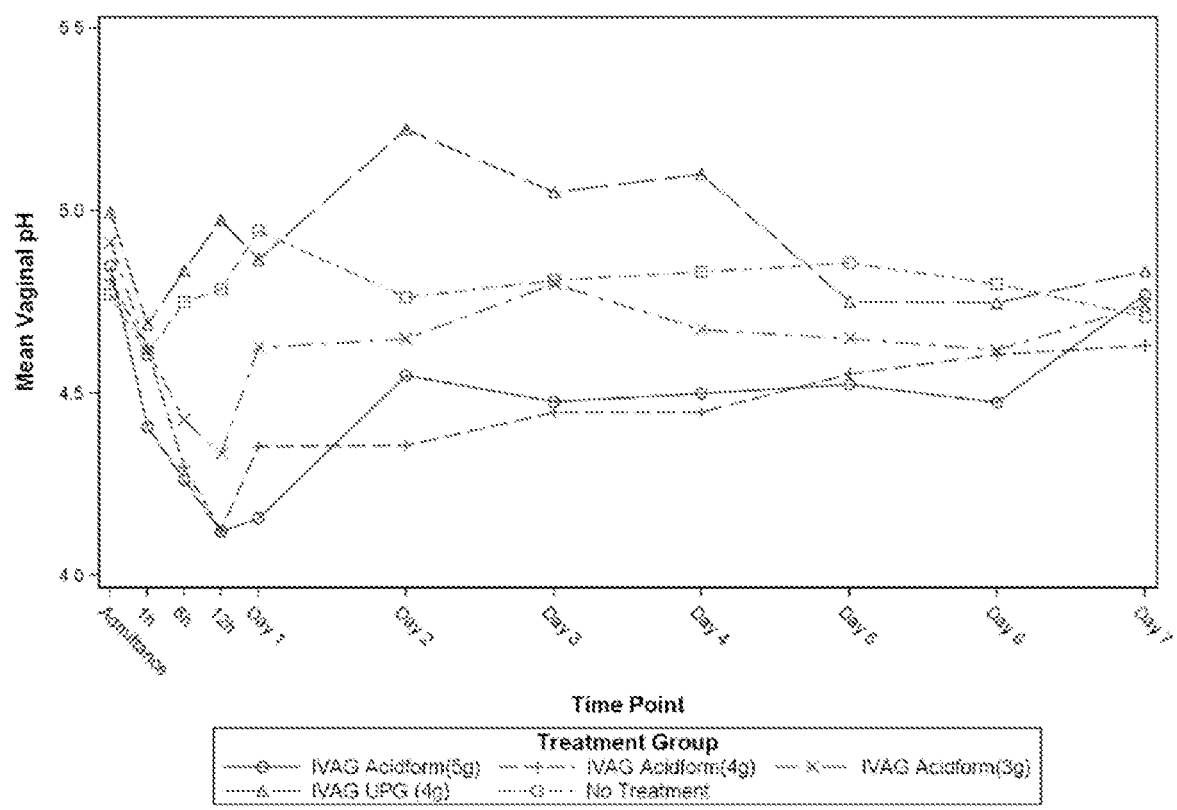
FIG. 3 is a graph illustrating mean vaginal pH at each assessment time point.
Figure 4:
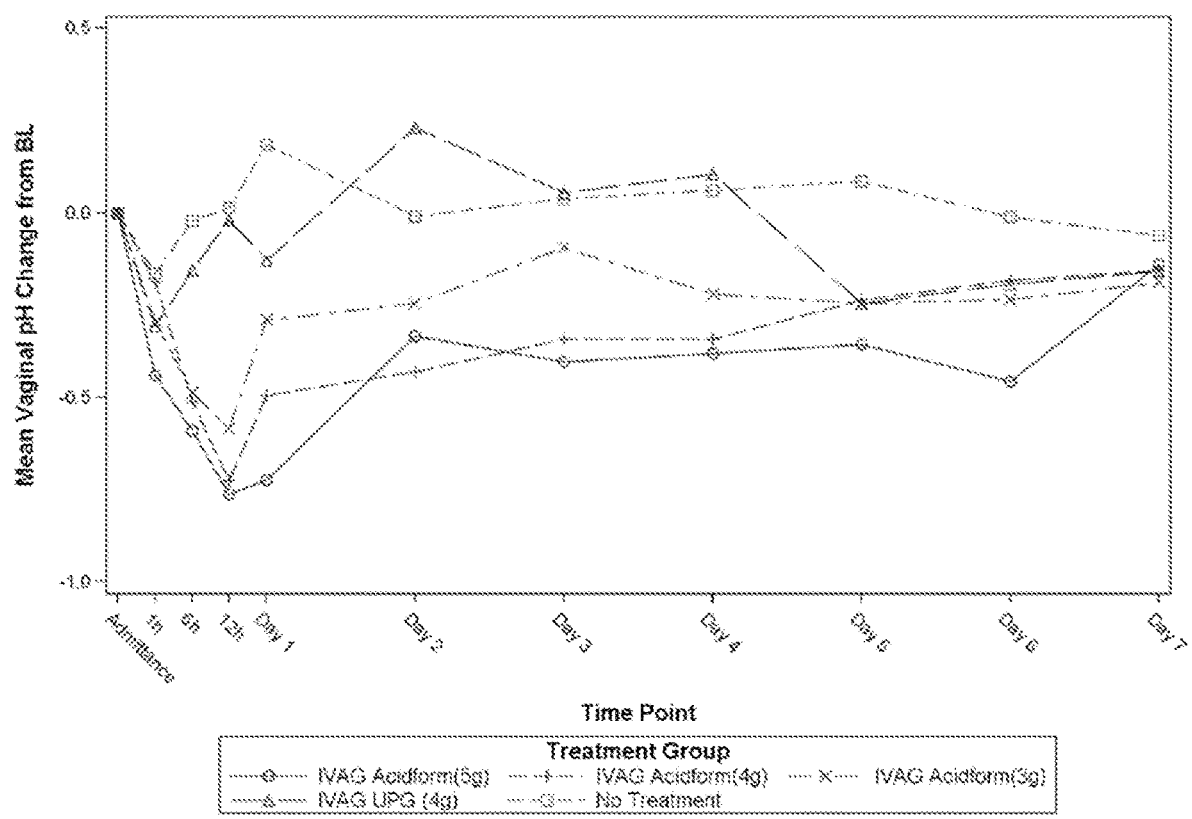
FIG. 4 is a graph illustrating mean change from baseline in vaginal pH at each assessment time point.
Figure 5:
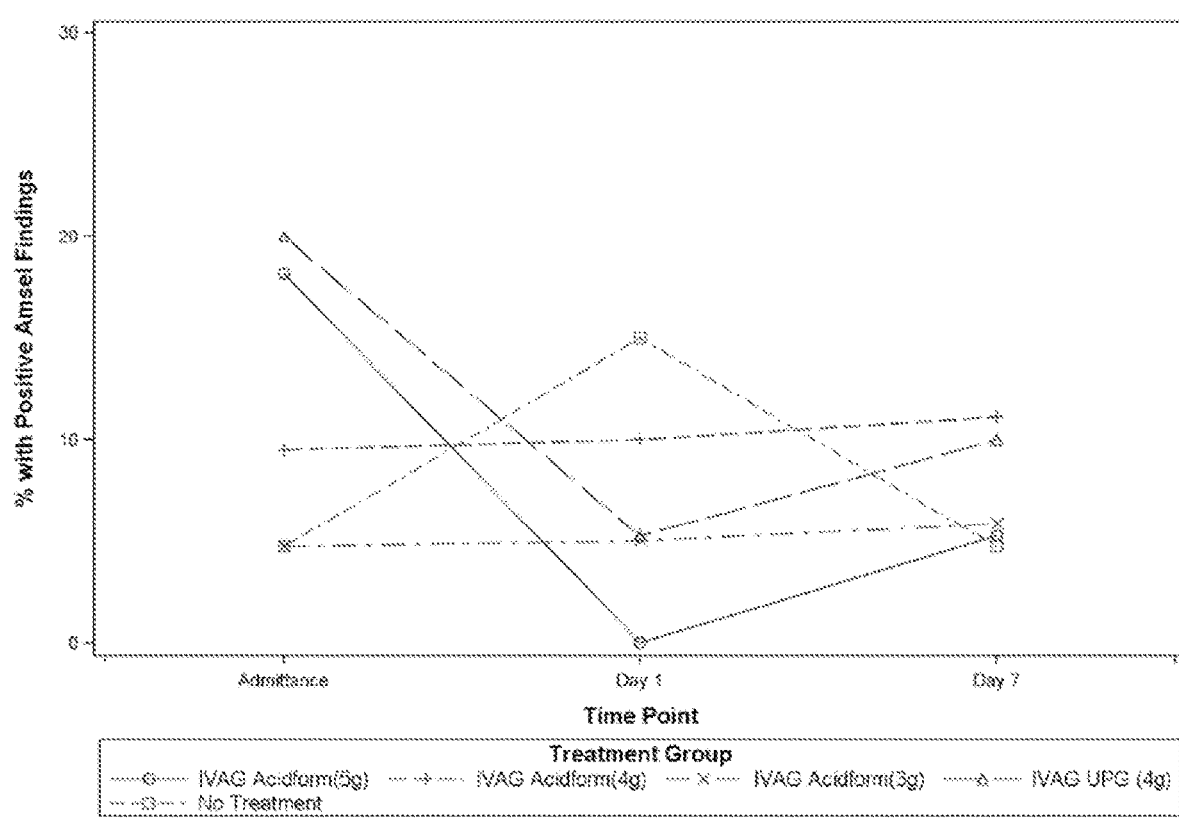
FIG. 5 is a graph illustrating percentage of subjects with positive overall Amsel results—all reporting subjects at each assessment timepoint.

Efficacy results showing the effect and duration of a single dose of IP (Acidform at either 5 g, 4 g, or 3 g), placebo 4 g, and no treatment on vaginal pH from baseline through to Day 7 (final study visit) are presented (FIG. 3 and FIG. 4).

Analysis of Efficacy

The mean vaginal pH for each treatment group and all assessment time points is shown in FIG. 3.

For those subjects who received placebo, mean vaginal pH fluctuated between 5.0 and 5.5, where subjects receiving no treatment had a mean vaginal pH around 4.8 to 4.7. In contrast, all subjects receiving Acidform at any dose had a noticeable decline in mean vaginal pH, within 12 hours of the administration compared to the baseline pH measurements taken at the time of administration. It was observed that the mean vaginal pH for subjects in any of the 3 Acidform treatment groups remained lower than the mean vaginal pH of the no-treatment and the placebo groups, up to Day 6 following administration. The greatest reductions in mean vaginal pH were seen with Acidform at the 5 g and 4 g doses.

The mean change in vaginal pH from baseline through to Day 7, including all intermediary time points, was recorded. These results formed part of the exploratory analysis to measure the duration of effect of a single dose of IP (Acidform at either 5 g, 4 g, or 3 g dose), placebo 4 g, and no treatment on vaginal pH (see FIG. 4).

For subjects who received the placebo or no treatment, no noticeable mean change in vaginal pH from baseline (measurements taken at the time of administration) was observed. In contrast, all subjects receiving Acidform had a noticeable mean change in vaginal pH from the time of administration of Acidform to 12 hours compared to the baseline pH measurements taken at the time of administration. The mean change in vaginal pH compared to baseline for subjects in any of the 3 Acidform treatment groups remained noticeable compared to the mean change in vaginal pH from baseline of the no treatment and the placebo group. The greatest reductions in mean vaginal pH were seen with Acidform at the 5 g and 4 g doses. (FIG. 4).

Assessment of the effect of a single dose of Acidform or placebo, or no treatment on asymptomatic BV based on Amsel criteria, was assessed as an exploratory endpoint. Results of these findings were assessed on subject admittance, Day 1 and Day 7. Although 4 of 22 (19%) of subjects in the Acidform 5 g treatment group had positive Amsel findings at baseline, none had positive Amsel findings at Day 1. By Day 7, 1 of 22 (5%) had positive Amsel findings. This finding suggests Acidform 5 g prevents recurrence of BV infection, at least in the short term.

Adjustments for Covariates

The comparison across study treatments with respect to changes from baseline vaginal pH values explored the use of baseline pH as a covariate. Other than this possible application, no adjustments were planned for this study.

Handling of Dropouts or Missing Data

No imputation of missing data values was performed. All analyses were based on data as observed.

Efficacy Results

A single dose of Acidform at any of the 3 studied doses lowered vaginal pH from baseline, and this mean reduction was significantly greater than that seen with placebo or no treatment. Peak reduction occurred at 12-hours post-administration, with the greatest reduction in mean vaginal pH from baseline seen with the highest (5 g) dose. Subjects in the Acidform treatment groups continued to have a lower mean vaginal pH at Day 6 compared to the mean vaginal pH of subjects in the placebo and the no-treatment group. Subjects in the Acidform treatment groups continued to have mean reduction in vaginal pH at Day 7 compared to baseline.

Safety Evaluation

A global summary of demographics of the safety population is presented in Table 8. A detailed summary of AEs, including subjects with at least one treatment-emergent adverse event (TEAE), treatment-related AEs, SAEs, and AEs leading to study withdrawal during the 7-day double-blind treatment period of the study is presented in Table 9. The incidence of AEs by body system organ class and preferred term is summarized in Table 8 for the treatment period. There were no SAEs reported in this study and no AEs led to study withdrawal during the treatment period.

AEs are reported using MedDRA® (Version 17.0 or higher).

Extent of Exposure

A total of 105 subjects participated in this study and were randomized across 5 treatment groups. Of the 105 subjects, only 84 received treatment (including placebo) as 21 subjects were assigned to the no-treatment group. As this was a single dose study, all subjects enrolled were included in the safety population (Table 8).

Adverse Events

Brief Summary of Adverse Events

Sixty-eight subjects (64.8%) reported a TEAE, none of which were serious, severe or lifethreatening, and did not lead to study discontinuation. TEAEs ranged from 61.9% to 76.2% across the treatment groups including IP or placebo, and was 47.6% in the no-treatment group.

Three subjects (14.3%) in the no-treatment group were assessed by study clinicians as having a treatment-related TEAE, which is explained by the fact that this was a double-blind study and could imply that some TEAEs experienced by subjects are naturally experienced by females over time.

Gel-associated "discharge" peaked on Day 2 and declined thereafter, and is best explained by leakage of some of the gel over time.

TABLE 8

Overview of Treatment-Emergent Adverse Events (Safety Population)

| Category | Acidform (5 g) n = 22 | Acidform (4 g) n = 21 | Acidform (3 g) n = 21 | Placebo (4 g) n = 20 | No-Treatment n = 21 |
|---|---|---|---|---|---|
| TEAEs | 16 (72.7%) | 13 (61.9%) | 16 (76.2%) | 13 (65.0%) | 10 (47.6%) |
| Treatment-Related TEAEs[1] | 12 (54.5%) | 8 (38.1%) | 11 (52.4%) | 7 (35.0%) | 3 (14.3%) |
| Severe or Life-Threatening TEAEs | 0 | 0 | 0 | 0 | 0 |
| Serious TEAEs | 0 | 0 | 0 | 0 | 0 |
| Serious, Treatment-Related TEAEs | 0 | 0 | 0 | 0 | 0 |
| TEAEs Leading to Study Treatment Modification or Discontinuation from Study | 0 | 0 | 0 | 0 | 0 |

TEAE = Treatment-Emergent Adverse Event
[1]Included TEAEs were considered by the Investigator to be probably or definitely related to the study drug. Subjects may have more than one AE per category. For each category, a subject was counted once if she reported one or more events. Percentages are based on the number of subjects in the indicated treatment group. The Safety Population included all subjects who received any amount of study treatment, and all subjects who were randomized to the no-treatment group.

TABLE 9

Overview of Treatment-Emergent Adverse Events by System Organ Class (Safety Population)

| System Organ Class Preferred Term | Acidform (5 g) n = 22 | Acidform (4 g) n = 21 | Acidform (3 g) n = 21 | Placebo (4 g) n = 20 | No-Treatment n = 21 |
|---|---|---|---|---|---|
| Total Number of AEs | 34 | 28 | 32 | 26 | 13 |
| Total Number of Subjects with at Least One AE | 16 (72.7%) | 13 (61.9%) | 16 (76.2%) | 13 (65.0%) | 10 (47.6%) |
| Infections and Infestations | 1 (4.5%) | 0 | 0 | 0 | 1 (4.8%) |
| Nasopharyngitis | 0 | 0 | 0 | 0 | 1 (4.8%) |
| Urinary Tract Infection | 1 (4.5%) | 0 | 0 | 0 | 0 |
| Musculoskeletal and connective tissue disorders | 1 (4.5%) | 0 | 0 | 0 | 0 |
| Muscle spasms | 1 (4.5%) | 0 | 0 | 0 | 0 |
| Nervous system disorders | 2 (9.1%) | 0 | 0 | 1 (5.0%) | 1 (4.8%) |
| Headache | 1 (4.5%) | 0 | 0 | 1 (5.0%) | 1 (4.8%) |
| Sciatica | 1 (4.5%) | 0 | 0 | 0 | 0 |
| Total Number of AEs | 34 | 28 | 32 | 26 | 13 |
| Renal and urinary disorders | 0 | 1 (4.8%) | 1 (4.8%) | 0 | 0 |
| Micturition urgency | 0 | 1 (4.8%) | 0 | 0 | 0 |
| Pollakiuria | 0 | 0 | 1 (4.8%) | 0 | 0 |
| Reproductive system and breast disorders | 16 (72.7%) | 13 (61.9%) | 16 (76.2%) | 13 (65.0%) | 9 (42.9%) |
| Cervical discharge | 1 (4.5%) | 1 (4.8%) | 2 (9.5%) | 2 (10.0%) | 3 (14.3%) |
| Cervix disorder | 1 (4.5%) | 0 | 1 (4.8%) | 2 (10.0%) | 1 (4.8%) |
| Cervix inflammation | 0 | 0 | 1 (4.8%) | 0 | 0 |
| Dysmenorrhea | 0 | 2 (9.5%) | 0 | 0 | 0 |
| Menstruation irregular | 1 (4.5%) | 0 | 1 (4.8%) | 0 | 0 |
| Vaginal discharge | 15 (68.2%) | 13 (61.9%) | 12 (57.1%) | 10 (50.0%) | 3 (14.3%) |
| Vaginal hemorrhage | 0 | 1 (4.8%) | 1 (4.8%) | 3 (15.0%) | 1 (4.8%) |
| Vaginal odor | 0 | 0 | 2 (9.5%) | 0 | 0 |
| Vulvovaginal burning sensation | 1 (4.5%) | 0 | 1 (4.8%) | 0 | 0 |
| Vulvovaginal discomfort | 1 (4.5%) | 0 | 2 (9.5%) | 0 | 0 |
| Vulvovaginal pain | 1 (4.5%) | 1 (4.8%) | 0 | 1 (5.0%) | 2 (9.5%) |
| Vulvovaginal pruritis | 3 (13.6%) | 2 (9.5%) | 1 (4.8%) | 3 (15.0%) | 0 |

The total number of AEs counts all AEs for all subjects. Subjects may have more than one AE per body system and preferred term.
At each level of subject summarization, a subject was counted once if she reported one or more events.
Percentages are based on the number of subjects in the indicated treatment group.
AE = adverse event.

Display of Adverse Events

The most common AE across all treatment groups was vaginal discharge (Table 9). This finding was noted in the majority of subjects who received IP (Acidform at any dose or placebo), ranging from 50.0% to 68.2%, and 14.3% of subjects in the no-treatment group (Table 9).

No other frequent AEs were noted or were of any cause for concern.

Adverse Events by Severity

All AEs reported in this study were mild to moderate, across all treatment groups: the majority were classified as mild.

Relationship of Adverse Event to Study Drug

AE rates were similar across the four treatment groups, but were lower for the no-treatment group. There appeared to be no significant difference in AE frequency or severity between the 3 doses of Acidform (5 g, 4 g, and 3 g), or between the 3 doses of Acidform and placebo.

Severity of Adverse Events Related to Study Drug

All related AEs reported in this study were mild to moderate, across all treatment groups.

Deaths, Other Serious Adverse Events, and Other Significant Adverse Events

There were no deaths, SAEs, or other significant AEs reported in this study.

Safety Conclusions

Sixty-eight subjects (64.8%) reported a TEAE, none of which were serious, severe or life-threatening. The most common AE across all treatment groups was vaginal discharge, which was higher among subjects receiving IP (Acidform at either 5 g, 4 g, or 3 g, or placebo) compared with subjects receiving no treatment. Administration of gel, both placebo and Acidform, resulted in leakage of some gel over time that was experienced as "discharge", which diminished over time.

No deaths or SAEs were reported in this study. All reported TEAEs were mild or moderate and did not require concomitant treatment or lead to study discontinuation.

Discussion and Overall Study Conclusions

Vaginal pH was lowered from baseline with a single dose of Acidform at the 3 studied dosages (5 g, 4 g, and 3 g). The mean reduction was significantly greater than reductions in vaginal pH seen with either placebo or no treatment. Peak reduction occurred 12-hours post-administration of Acidform, with the greatest reduction in mean vaginal pH from baseline seen with the highest (5 g) dose. Subjects in the Acidform treatment groups continued to have mean reduction in vaginal pH at Day 7 compared to baseline.

CERTAIN EMBODIMENTS

Embodiment 1 provides a method of treating bacterial vaginosis (BV) comprising intravaginally administering a composition to a subject with BV, wherein the composition comprises: (a) a polymer thickener; (b) L-lactic acid; and (c) a preservative, wherein administering the composition ameliorates symptoms of BV in the subject.

Embodiment 2 provides a method of reducing the recurrence rate of bacterial vaginosis (BV) comprising intravaginally administering a composition to a subject with BV, wherein the composition comprises: (a) a polymer thickener; (b) L-lactic acid; and (c) a preservative, wherein administering the composition reduces recurrence rate of bacterial vaginosis in the subject.

Embodiment 3 provides a method of preventing the recurrence of bacterial vaginosis (BV) comprising intravaginally administering a composition to a subject with BV, wherein the composition comprises: (a) a polymer thickener; (b) L-lactic acid; and (c) a preservative, wherein administering the composition prevents recurrence of bacterial vaginosis in the subject.

Embodiment 4 provides the method of any one of embodiments 1-3, wherein the preservative is selected from a group consisting of benzoic acid, sodium benzoate, methylparaben, ethylparaben, butyulparaben, propylparaben, benzyalkonium chloride, phenylmercuric nitate, and chlorhexidine.

Embodiment 5 provides the method of any one of embodiments 1-4, wherein the polymer thickener is selected from a group consisting of xanthan gum, alginic acid, hydroxypropyl cellulose, hydroxypropyl methyl cellulose, sodium carboxymethyl cellulose, chitosan, polycarbophil, and carbopol.

Embodiment 6 provides the method of any one of embodiments 1-5, wherein the polymer thickener is a combination of xanthan gum and alginic acid.

Embodiment 7 provides the method of any one of embodiments 1-6, wherein the composition further comprises a humectant.

Embodiment 8 provides the method of any one of embodiments 1-7, wherein the humectant is selected from a group consisting of glycerol, polyethylene glycol, propylene glycol, sorbitol, and tiracetin.

Embodiment 9 provides the method of any one of embodiments 1-8, wherein the composition further comprises a pharmaceutically acceptable carrier.

Embodiment 10 provides the method of any one of embodiments 1-9, wherein the composition further comprises water.

Embodiment 11 provides the method of any one of embodiments 1-10, wherein the composition further comprises a buffer.

Embodiment 12 provides the method of any one of embodiments 1-11, wherein the buffer comprises citric acid and potassium bitartrate.

Embodiment 13 provides the method of any one of embodiments 1-12, wherein the composition is administered once during a course of treatment.

Embodiment 14 provides the method of any one of embodiments 1-12, wherein the composition is administered multiple times during a course of treatment.

Embodiment 15 provides the method of embodiment 14, wherein the course of treatment comprises an initial course of treatment and a subsequent course of treatment and wherein the composition is administered more frequently during the initial course of treatment than during the subsequent course of treatment.

Embodiment 16 provides the method of embodiment 15, wherein the initial course of treatment is between 1 week and 4 weeks.

Embodiment 17 provides the method of embodiment 16, wherein the initial course of treatment is about 2 weeks to about 3 weeks.

Embodiment 18 provides the method of embodiment 17, wherein the initial course of treatment is about 1 week.

Embodiment 19 provides the method of any one of embodiments 15-18, wherein the subsequent course of treatment is about 1 week to about 19 weeks.

Embodiment 20 provides the method of any one of embodiments 15-19, wherein the subsequent course of treatment is about 2 weeks to about 18 weeks.

Embodiment 21 provides the method of any one of embodiments 15-20, wherein the subsequent course of treatment is about 3 weeks to about 17 weeks.

Embodiment 22 provides the method of any one of embodiments 15-21, wherein the subsequent course of treatment is about 4 weeks to about 16 weeks.

Embodiment 23 provides the method of any one embodiments 15-22, wherein the subsequent course of treatment is 5 weeks to about 15 weeks.

Embodiment 24 provides the method of any one of embodiments 15-23, wherein the subsequent course of treatment is about 6 weeks to about 14 weeks.

Embodiment 25 provides the method of any one of embodiments 15-24, wherein the subsequent course of treatment is about 7 weeks to about 13 weeks.

Embodiment 26 provides the method of any one of embodiments 15-25, wherein the subsequent course of treatment is about 8 weeks to about 12 weeks.

Embodiment 27 provides the method of any one of embodiments 15-26, wherein the subsequent course of treatment is about 9 weeks to about 10 weeks.

Embodiment 28 provides the method of any one of embodiments 15-27, wherein the subsequent course of treatment is about 10 weeks to about 11 weeks.

Embodiment 29 provides the method of any one of embodiments 15-28, wherein the frequency of administration during the initial course of treatment is daily.

Embodiment 30 provides the method of any one of embodiments 15-29, wherein the frequency of administration during the initial course of treatment is every other day.

Embodiment 31 provides the method of any one of embodiments 15-30, wherein the frequency of administration during the initial course of treatment is once a week.

Embodiment 32 provides the method of any one of embodiments 15-31, wherein the frequency of administration during the initial course of treatment is once every 2 weeks.

Embodiment 33 provides the method of any one of embodiments 15-32, wherein the frequency of administration during the subsequent course of treatment is every other day.

Embodiment 34 provides the method of any one of embodiments 15-33, wherein the frequency of administration during the initial course of treatment is once every week.

Embodiment 35 provides the method of any one of embodiments 15-34, wherein the frequency of administration during the initial course of treatment is once every 2 weeks.

Embodiment 36 provides the method of any one of embodiments 15-35, wherein the frequency of administration during the initial course of treatment is once every 3 weeks.

Embodiment 37 provides the method of any one of embodiments 1-36, wherein the composition is administered at a dosage from about 0.5 g to about 10 g.

Embodiment 38 provides the method of any one of embodiments 1-37, wherein the composition is administered at a dosage from about 3 g to about 5 g.

Embodiment 39 provides the method of any one of embodiments 1-38, wherein the composition is administered at a dosage selected from about 3 g, about 4 g, and about 5 g.

Embodiment 40 provides a method of prognosis for risk of recurrence of bacterial vaginosis (BV) in a subject with BV, the method comprising (a) testing vaginal pH of the subject; (b) intravaginally administering a composition as defined in any one of embodiments 1-12 to the subject, (c) re-testing vaginal pH of the subject; and (d) prognosing risk of recurrence of BV based on comparing the results of the vaginal pH tests in step (a) and (c).

Embodiment 41 provides a method of prognosis for risk of recurrence of bacterial vaginosis (BV) in a subject with BV, the method comprising (a) analyzing vaginal microbiome of the subject; (b) intravaginally administering a composition as defined in any one of embodiments 1-12 to the subject, (c) re-analyzing vaginal microbiome of the subject; and (d) prognosing risk of recurrence of BV based on comparing the results of the vaginal microbiome analyses in step (a) and (c).

Embodiment 42 provides a method of prognosis for risk of recurrence of bacterial vaginosis (BV) in a subject, the method comprising (a) assessing BV in a subject using Amsel criteria; (b) intravaginally administering a composition as defined in any one of embodiments 1-12 to the subject, (c) re-assessing BV in the subject using Amsel criteria; and (d) prognosing risk of recurrence of BV based on comparing the assessments in step (a) and (c).

Embodiment 43 provides the method of any one of embodiments 40-42, wherein the composition is administered once during a course of treatment.

Embodiment 44 provides the method of any one of embodiments 40-42, wherein the composition is administered multiple times during a course of treatment.

Embodiment 45 provides the method of embodiment 44, wherein the course of treatment comprises an initial course of treatment and a subsequent course of treatment and wherein the composition is administered more frequently during the initial course of treatment than during the subsequent course of treatment.

Embodiment 46 provides the method of embodiment 45, wherein the initial course of treatment is between 1 week and 4 weeks.

Embodiment 47 provides the method of embodiment 45, wherein the initial course of treatment is about 2 weeks to about 3 weeks.

Embodiment 48 provides the method of embodiment 47, wherein the initial course of treatment is about 1 week.

Embodiment 49 provides the method of any one of embodiments 45-48, wherein the subsequent course of treatment is about 1 week to about 19 weeks.

Embodiment 50 provides the method of any one of embodiments 45-49, wherein the subsequent course of treatment is about 2 weeks to about 18 weeks.

Embodiment 51 provides the method of any one of embodiments 45-50, wherein the subsequent course of treatment is about 3 weeks to about 17 weeks.

Embodiment 52 provides the method of any one of embodiments 45-51, wherein the subsequent course of treatment is about 4 weeks to about 16 weeks.

Embodiment 53 provides the method of any one embodiments 45-52, wherein the subsequent course of treatment is 5 weeks to about 15 weeks.

Embodiment 54 provides the method of any one of embodiments 45-53, wherein the subsequent course of treatment is about 6 weeks to about 14 weeks.

Embodiment 55 provides the method of any one of embodiments 45-54, wherein the subsequent course of treatment is about 7 weeks to about 13 weeks.

Embodiment 56 provides the method of any one of embodiments 45-55, wherein the subsequent course of treatment is about 8 weeks to about 12 weeks.

Embodiment 57 provides the method of any one of embodiments 45-56, wherein the subsequent course of treatment is about 9 weeks to about 10 weeks.

Embodiment 58 provides the method of any one of embodiments 45-57, wherein the subsequent course of treatment is about 10 weeks to about 11 weeks.

Embodiment 59 provides the method of any one of embodiments 45-58, wherein the frequency of administration during the initial course of treatment is daily.

Embodiment 60 provides the method of any one of embodiments 45-59, wherein the frequency of administration during the initial course of treatment is every other day.

Embodiment 61 provides the method of any one of embodiments 45-60, wherein the frequency of administration during the initial course of treatment is once a week.

Embodiment 62 provides the method of any one of embodiments 45-61, wherein the frequency of administration during the initial course of treatment is once every 2 weeks.

Embodiment 63 provides the method of any one of embodiments 45-62, wherein the frequency of administration during the subsequent course of treatment is every other day.

Embodiment 64 provides the method of any one of embodiments 45-63, wherein the frequency of administration during the initial course of treatment is once every week.

Embodiment 65 provides the method of any one of embodiments 45-64, wherein the frequency of administration during the initial course of treatment is once every 2 weeks.

Embodiment 66 provides the method of any one of embodiments 45-65, wherein the frequency of administration during the initial course of treatment is once every 3 weeks.

Embodiment 67 provides the method of any one of embodiments 40-66, wherein the composition is administered at a dosage from about 0.5 g to about 10 g.

Embodiment 68 provides the method of any one of embodiments 40-67, wherein the composition is administered at a dosage from about 3 g to about 5 g.

Embodiment 69 provides the method of any one of embodiments 40-68, wherein the composition is administered at a dosage selected from about 3 g, about 4 g, and about 5 g.

Embodiment 70 provides the method of any one of embodiments 40 and 43-69, wherein lowering of vaginal pH between steps (a) and (c) is associated with good prognosis for reduced risk of recurrence of BV.

Embodiment 71 provides the method of any one of embodiments 41 and 43-69, wherein restoration of a healthy vaginal microbiome between steps (a) and (c) is associated with good prognosis for reduced risk of recurrence of BV.

Embodiment 72 provides the method of any one of embodiments 42-69, wherein the assessment result is Amsel-positive or Amsel-negative in the steps (a) and (c).

Embodiment 73 provides the method of embodiments 72, wherein change in assessment result from Amsel-positive to Amsel-negative between steps (a) and (c) is associated with good prognosis for reduced risk of recurrence of BV.

What is claimed is:

1. A method of treating bacterial vaginosis (BV) comprising intravaginally administering a composition to a subject with BV, wherein the composition consists of: (a) a polymer thickener; (b) about 2.5% w/v L-lactic acid; (c) a preservative, (d) citric acid, (e) potassium bitartrate, (f) a humectant, (g) a pH adjusting agent, and (h) a solvent, wherein the composition is administered multiple times during a course of treatment, wherein the course of treatment comprises about 1 week to about 20 weeks, wherein the composition is administered at a dosage from about 0.5 g to about 10 g per dose, and wherein administering the composition ameliorates symptoms of BV in the subject.

2. The method of claim 1, wherein the polymer thickener is selected from a group consisting of xanthan gum, alginic acid, hydroxypropyl cellulose, hydroxypropyl methyl cellulose, sodium carboxymethyl cellulose, chitosan, polycarbophil, and carbopol.

3. The method of claim 1, wherein the solvent is water.

4. The method of claim 1, wherein the course of treatment comprises an initial course of treatment and a subsequent course of treatment and wherein the composition is administered more frequently during the initial course of treatment than during the subsequent course of treatment.

5. The method of claim 4, wherein the frequency of administration during the initial course of treatment is daily, less than once daily, every other day, once a week, or once every 2 weeks.

6. The method of claim 4, wherein the frequency of administration during the subsequent course of treatment is less than once daily, every other day, once a week, once every 2 weeks, or once every 3 weeks.

7. The method of claim 1, wherein the composition is administered at a dosage from about 3 g to about 5 g, about 3 g, about 4 g, or about 5 g.

8. The method of claim 1, wherein the subject has previously been diagnosed as Amsel-positive.

9. The method of claim 8, wherein upon of administration of the composition the subject is Amsel-negative, thereby treating the BV.

10. A method of reducing the recurrence rate of bacterial vaginosis (BV) comprising intravaginally administering a composition to a subject, wherein the composition consists of: (a) a polymer thickener; (b) about 2.5% w/v L-lactic acid; (c) a preservative, (d) citric acid, (e) potassium bitartrate, (f) of a humectant, (g) a pH adjusting agent, and (h) a solvent, wherein the composition is administered multiple times during a course of treatment, wherein the course of treatment comprises about 1 week to about 20 weeks, wherein the composition is administered at a dosage from about 0.5 g to about 10 g per dose, and wherein administering the composition reduces recurrence rate of bacterial vaginosis in the subject.

11. The method of claim 10, wherein the subject is a subject with BV.

12. The method of claim 11, wherein the subject with BV is asymptomatic.

13. The method of claim 10, wherein the subject is free of BV.

14. The method of claim 10, wherein the polymer thickener is selected from a group consisting of xanthan gum, alginic acid, hydroxypropyl cellulose, hydroxypropyl methyl cellulose, sodium carboxymethyl cellulose, chitosan, polycarbophil, and carbopol.

15. The method of claim 10, wherein the solvent is water.

16. The method of claim 10, wherein the course of treatment comprises an initial course of treatment and a subsequent course of treatment and wherein the composition is administered more frequently during the initial course of treatment than during the subsequent course of treatment.

17. The method of claim 16, wherein the frequency of administration during the initial course of treatment is daily, less than once daily, every other day, once a week, or once every 2 weeks.

18. The method of claim 16, wherein the frequency of administration during the subsequent course of treatment is less than once daily, every other day, once a week, once every 2 weeks, or once every 3 weeks.

19. The method of claim 10, wherein the composition is administered at a dosage from about 3 g to about 5 g, about 3 g, about 4 g, or about 5 g.

20. The method of claim 1, wherein a pH less than 5 is maintained in the vagina.

21. The method of claim 10, wherein a pH less than 5 is maintained in the vagina.

* * * * *